United States Patent [19]

Ugarkar et al.

[11] Patent Number: 5,721,356

[45] Date of Patent: Feb. 24, 1998

[54] ORALLY ACTIVE ADENOSINE KINASE INHIBITORS

[75] Inventors: Bheemarao G. Ugarkar, Escondido; Mark D. Erion, Del Mar; Jorge E. Gomez Galeno, La Jolla; Angelo J. Castellino, San Diego, all of Calif.; Clinton E. Browne, Gainesville, Fla.

[73] Assignee: Gensia, Inc., San Diego, Calif.

[21] Appl. No.: 473,491

[22] Filed: Jun. 7, 1995

Related U.S. Application Data

[63] Continuation-in-part of Ser. No. 812,916, Dec. 23, 1991, abandoned, which is a continuation-in-part of Ser. No. 647,117, Jan. 23, 1991, abandoned, which is a continuation-in-part of Ser. No. 466,979, Jan. 18, 1990, abandoned, which is a continuation-in-part of Ser. No. 408,707, Sep. 15, 1989, abandoned.

[51] Int. Cl.$^6$ .................................................. C07H 19/16
[52] U.S. Cl. .................. 536/27.2; 536/27.21; 536/27.22; 536/27.62; 536/27.7
[58] Field of Search ........................ 536/27.2, 27.21, 536/27.22, 27.62, 27.7

[56] References Cited

U.S. PATENT DOCUMENTS

| | | | |
|---|---|---|---|
| 3,309,358 | 3/1967 | Hanze et al. | 536/27.2 |
| 3,962,211 | 6/1976 | Townsend et al. | 536/27.2 |
| 4,352,795 | 10/1982 | Cook | 536/27.2 |
| 4,439,604 | 3/1984 | Cook | 536/27.2 |
| 4,455,420 | 6/1984 | Kazlauskas . | |
| 4,904,666 | 2/1990 | Friebe et al. . | |
| 5,446,139 | 8/1995 | Seela et al. | 536/27.21 |
| 5,506,347 | 4/1996 | Erion et al. | 536/27.2 |

FOREIGN PATENT DOCUMENTS

| | | |
|---|---|---|
| 0286028 | 4/1987 | European Pat. Off. . |
| 0 496 617 A | 7/1992 | European Pat. Off. . |
| 3931557 | 9/1989 | Germany . |
| 9003370 | 4/1990 | WIPO . |
| WO 94/17803 | 8/1993 | WIPO . |
| WO 94/18215 | 8/1994 | WIPO . |

OTHER PUBLICATIONS

Achterberg, Peter W., et al., *Biochem. J.* (1986) 235, 13–17.
Bontemps, Francoise et al., *Proc. Natl. Acad. Sci. USA* vol. 80, pp. 2829–2833, May 1983 Biochemistry.
Burke, Stephan P. et al., *Journal of Neurochemistry*, vol. 51, No. 5, 1988.
Caldwell, Ian C., et al. *Cancer Chemotherapy Reports* (Part 2) vol. 2, No. 1, Apr. 1971.
Cheng, C.C., et al., *The Journal of Organic Chemistry* vol. 21, No. 11, Nov. 1956.
Cottam, Howard B., et al., *J. Med. Chem.* 1984, 27, 1119–1127.
Davies, Les P., et al. *Biochemistry Pharmacology*, vol. 33, No. 3, pp. 347–355, 1984.
Davies, Les P., et al. *Biochemical Pharmacology*, vol. 35, No. 18, pp. 3021–3029, 1986.
Firestein, Gary S., et al. *The Journal of Immunology*, 1995, 154, 326–334.
Flynn, Bernard L., et al. *Nucleosides & Nucleotides*, 10(4), 763–779 (1991).
Green, Richard D. *Journal of Supramolecular Structure* 13:175–182 (1980) Membrane Transport & Neuroreceptors 109–116.
Henderson, J.F., et al. *Cancer Chemotherapy Reports*, Part 2, vol. 3:71–85 No. 1, Nov. 1972.
Keil II, G.J., et al. *Life Sciences*, vol. 51, pp. PL 171–176 (1992).
Kobayashi, Shigeru, *Chem. Pharm. Bull.*, 21(5) 941–951 (1973).
Miller, Richard L., et al., *The Journal of Biological Chemistry*, vol. 254, No. 7 (1979) pp. 2346–2352.
Newby, Andrew C., et al. *Biochem. J.*, (1983) 214, 317–323.
Pak, M.A. et al., *Society for Neuroscience Abstracts*, vol. 20, 1994.
Prescott, M. et al., *Nucleosides & Nucleotides*, 8(2), 297–303 (1989).
Rosemeyer, Helmut et al., *Helvetica Chimica Acta*, vol. 71 (1988) pp. 1573–1585.
Rosengren, Sanna, et al., *The Journal of Immunology*, 1995, 154:5444–5451.
Sciotti, Veronica M., et al., *Journal of Cerebral Blood Flow & Metabolism*, 13:201–207 (1993).
Snyder, Joseph R., et al., *Carbohydrate Research*, 163 (1987) 169–188.
Sosnowski, M., et al., *The Journal of Pharmacology & Experimental Therapeutics*, vol. 250, No. 3 (1989).
Swinyard, Ewart A. et al., *Antiepileptic Drugs, Third Edition* (1989) pp. 85–102.
White, I.D., *Society for Neuroscience Abstracts*, vol. 20, 1994.
Wu, Shi-Qu, et al., *Cytobios*, 50 7–12, 1987.
Yamada, Yasukazu et al., *Biochimica et Biophysica Acta*, 660 (1981) 36–43.
Phillis, John W., et al., *Life Sciences*, vol. 53, pp. 497–502 (1993).
Zoref-Shani, Esther, et al.,*Mol Cell Cardiol*, 20, 23–33 (1988).

*Primary Examiner*—James O. Wilson
*Attorney, Agent, or Firm*—Darby & Darby

[57] ABSTRACT

This invention relates to adenosine kinase inhibitors and to nucleoside analogs, specifically to orally active, substituted 5-aryl pyrrolo[2,3-d]pyrimidine and 3-aryl pyrazolo[3,4-d] pyrimidine nucleoside analogs having activity as adenosine kinase inhibitors. The invention also relates to the preparation and use of these and other adenosine kinase inhibitors in the treatment of cardiovascular and cerebrovascular diseases, inflammation and other diseases which can be regulated by increasing the local concentration of adenosine.

57 Claims, No Drawings

ORALLY ACTIVE ADENOSINE KINASE INHIBITORS

This application is a continuation in part of U.S. patent application Ser. No. 07/812,916, filed Dec. 23, 1991, now abandoned, which is a continuation in part of U.S patent application Ser. No. 07/647,117, filed Jan. 23, 1991, now abandoned, which is a continuation in part of U.S. patent application Ser. No. 07/466,979, filed Jan. 18, 1990, now abandoned, which is a continuation in part of U.S. application Ser. No. 07/408,707, filed Sep. 15, 1989, now abandoned. The disclosure of these applications are incorporated herein by reference.

This invention relates to adenosine kinase inhibitors and to nucleoside analogs, specifically to orally active, substituted 5-aryl pyrrolo[2,3-d]pyrimidine and 3-aryl pyrazolo [3,4-d] pyrimidine nucleoside analogs having activity as adenosine kinase inhibitors. The invention also relates to the preparation and use of these and other adenosine kinase inhibitors in the treatment of cardiovascular and cerebrovascular diseases, inflammation and other diseases which can be regulated by increasing the local concentration of adenosine.

BACKGROUND OF THE INVENTION

Adenosine is an endogenously produced molecule that plays a major role in a variety of important cellular processes. It is a vasodilator, can inhibit immune function, enhance activation of mast cells (associated with allergic reactions), inhibit neutrophil oxygen free-radical production, is antiarrhythmic, and is an inhibitory neurotransmitter. Adenosine is phosphorylated to adenosine triphosphate (ATP) which is used by all cells to store energy for use in future energy-utilizing metabolic reactions or mechanical work (e.g. muscle contraction). Extracellular adenosine, frequently prouced by breakdown of intracellular ATP pools, evokes a variety of pharmacological responses through activation of extracellular adenosine receptors located on the surface of nearly all cells. For example, adenosine produces a variety of cardiovascular related effects including vasodilation, inhibition of platelet aggregation, and negative inotropic, chronotropic and domotropic effects on the heart. Adenosine also has effects within the central nervous system (CNS) including inhibition of neurotransmitter release from presynaptic neurons and inhibition of post-synaptic neuron firing in brain and the spinal cord and at sites of inflammation, such as inhibition of neutrophil adhesion to endothelial cells and inhibition of neutrophil oxygen free-radical production.

Compounds that increase extracellular adenosine can be beneficial to living organisms, particularly under certain conditions. For example, compounds that increase adenosine levels have been associated with the treatment of ischemic conditions such as stroke, as well as other conditions benefitted by enhanced adenosine levels, such as inflammation, arthritis, seizures, epilepsy and other neurological conditions. The compounds are also useful for treating pain, as muscle relaxants, and for inducing sleep.

Adenosine kinase is a cytostolic enzyme which catalyzes the phosphorylation of adenosine to AMP. Inhibition of adenosine kinase can potentially reduce the ability of the cell to utilize adenosine, leading to increased adenosine outside of the cell where it is pharmacologically active. However, the regulation of adenosine concentration is complex and involves other adenosine-metabolizing enzymes each with different kinetic properties and mechanisms of regulation. Adenosine can also be deaminated to inosine by adenosine deaminase (ADA) and condensed with L-homocysteine to S-adenosylhomocysteine (SAH) by SAH hydrolase. The role of each of these enzymes in modulating adenosine concentration is dependent on the prevailing physiological conditions, is tissue specific and is not well understood.

A number of nucleosides including pyrrolo[2,3-d] pyrimidine and pyrazolo[3,4-d]pyrimidine analogs have been evaluated for inhibition of adenosine kinase but were reported to have $K_i$'s of greater than 800 nM. Caldwell and Henderson, *Cancer Chemother. Rep.*, 2:237–46 (1971); Miller et al., *J. Biol. Chem.*, 254:2346–52 (1979). A few compounds have been reported as potent inhibitors of adenosine kinase with $K_i$'s of less than 100 nM. These are the purine nucleosides,, 5'-amino-5'-deoxyadenosine (Miller et al.) and 1,12-bis(adenosin-$N^6$-yl)dodecane (Prescott et al., *Nucleosides & Nucleotides*, 8:297 (1989)); and the pyrrolopyrimidine nucleosides, 5-iodotubercidin (Henderson et al., *Cancer Chemotherapy Rep. Part 2*, 3:71–85 (1972); Bontemps et al., *Proc. Natl. Acad. Sci. USA*, 80:2829–33 (1983); Davies et al., *Biochem. Pharmacol.*, 35:3021–29 (1986)) and 5'-deoxy-5-iodotubercidin (Davies et al., *Biochem. Pharmacol.*, 33:347–55 (1984) and 35:3021–29 (1986)).

Some of these compounds have been used to evaluate whether adenosine kinase inhibition might lead to increased extracellular adenosine concentrations. In rat cardiomyocytes, inhibition of adenosine deaminase by 2'-deoxycoformycin was reported to have no effect on adenosine release from the cells. In contrast, inhibition of ADA together with adenosine kinase by 5'-amino-5'-deoxyadenosine resulted in a 6-fold increase in adenosine release. Zoref-Shani et al., *J. Mol. Cell. Cardiol.*, 20:23–33 (1988). The effects of the adenosine kinase inhibitor alone were not reported. Similar results were reported in isolated guinea pig hearts; in these studies addition of 5'-amino-5'-deoxyadenosine to the perfusion medium, in the presence of EHNA to inhibit deamination, was reported to result in a 15-fold increase of adenosine release. Schrader in *Regulatory Function of Adenosine;* (Berne et al.) eds. pp. 133–156 (1983). These effects were not apparent in the absence of ADA inhibition, and other studies using isolated rat hearts perfused with 5-iodotubercidin alone, have reported no increase in perfusate adenosine concentration under normoxic conditions Newby et al., *Biochem. J.*, 214:317–323 (1983), or under hypoxic, anoxic or ischemic conditions, Achtenberg et al., *Biochem. J.*, 235:13–17 (1986). In other studies, adenosine release has been measured in neuroblastoma cells in culture and compared with that of a variant deficient in adenosine kinase (AK$^-$). The AK$^-$ cells used in this study were said to release adenosine at an accelerated rate; the concentration of adenosine in the growth medium was reported to be elevated compared to the normal cells. Green, *J. Supramol. Structure*, 13:175–182 (1980). In rat and guinea pig brain slices, adenosine uptake was reportedly inhibited by the adenosine kinase inhibitors 5-iodotubercidin and 5'-deoxy-5-iodotubercidin. Davis et al., *Biochem. Pharmacol.*, 33:347–55 (1984). However, inhibition of uptake and intracellular trapping via phosphorylation does not necessarily result in increased extracellular adenosine, since the adenosine could enter other metabolic pathways or the percentage of adenosine being phosphorylated could be insignificant compared to the total adenosine removed.

The effects of adenosine and certain inhibitors of adenosine catabolism, including 5-iodotubercidin were evaluated in an experimental model in which dog hearts were subjected to ischemia and reperfusion; 5-iodotubericidin was reported to have inconsistent effects. Wu, et al., *Cytobios*, 50:7–12 (1987).

Although the adenosine kinase inhibitors, 5'-amino-5'-deoxyadenosine and 5-iodotubercidin have been widely used in experimental models, the susceptibility of 5'-amino-5'-deoxyadenosine to deamination, and hence its potentially short half life, and the cytotoxicity of 5-iodotubercidin make their clinical utility limited and may limit interpretations based on these compounds. The known pyrrolo[2,3-d] pyrimidines, 5-iodotubercidin and 5'-deoxy-5-iodotubercidin have been reported to cause pronounced general flaccidity and much-reduced spontaneous locomotor activity in mice, interpreted to be skeletal muscle relaxation; to cause hypothermia in mice; and to decrease blood pressure and heart rate in anesthetized rats. Daves et al., *Biochem. Pharmacol.*, 33:347–55 (1984) and 35:3021–29 (1986); and U.S. Pat. No. 4,455,420). The skeletal muscle effects of these compounds have been poorly documented, while the other effects were considered significant toxicities.

More recent references concerned with the mechanisms and effects of adenosine kinase inhibitors are Keil et al., *Life Sciences* 51:171–76 (1992); Zhang et al., *J. Pharmacol. Exper. Ther.* 264(3): 1415 (1993); Phillis et al., *Life Sciences*, 53:497–502 (1993); Sciotti et al., *J. Cerebral Blood Flow Metab.*, 13:201–207 (1993); Pak et al., *Soc. for Neuroscience Abs.*, 20:149.2 (1994); White, *Soc. Neurosci. Abs.*, 20:308.9 (1994); and Firestein et al., *J. Immunology* 154:326–34 (1995). These publications in general show that adenosine kinase inhibitors, as a class, have a role in brain functions, and show promise in connection with the treatment of neurological conditions such as seizures. One reference, Phillis et al., indicates that the known adenosine kinase inhibitor 5-iodotubercidin apparently does not protect against ischemic cerebral injury. Keil et al. disclose that adenosine kinase plays a key role in the mediation of nervous system responses to stimulus, particularly pain (antinociception), but notes that the control of endogenous adenosine concentrations by such means is a complex process requiring further study.

Thus, there is a need for selective, potent, and bioavailable adenosine kinase inhibitors with a useful half-life, i.e. compounds which can be exploited to beneficially influence or control endogenous adenosine kinase activity, and therefore, extracellular adenosine levels. The compounds of the invention are suitable adenosine kinase inhibitors having these characteristics.

SUMMARY OF THE INVENTION

The invention is directed to novel pyrrolo[2,3-d] pyrimidine and pyrazolo[3,4-d]pyrimidine nucleoside analogs. Preferred compounds are 4-amino pyrrolo[2,3-d] pyrimidine analogs that have an aryl substitutent at either or both the 4-amino group or the 5-position. Also preferred are 4-amino pyrazolo[3,4-d]spyrimidine analogs that have any aryl substituent at either or both the 4-amino group or the 3-position. Most preferred are the diaryl compounds, having an aryl group at both positions, particularly those where at least one aryl group is a substituted phenyl. It has been discovered that these compounds are highly selective adenosine kinase inhibitors with with oral bioavailability and oral efficacy significantly higher than other known known adenosine kinase inhibitors. The compounds are also nontoxic, particularly in connection with liver function.

The invention concerns the compounds themselves, the preparation of these compounds, and their in vitro and in vivo adenosine kinase inhibition activity of these compounds. Another aspect of the invention is directed to the clinical use of the compounds to increase adenosine concentrations in biological systems. For example, in vivo inhibition of adenosine kinase prevents phosphorylation of adenosine resulting in higher local concentrations of endogenous adenosine.

The compounds of the invention possess advantages for pharmaceutical use such as enhanced pharmacological selectivity, efficacy, bioavailability, ease of manufacture and compound stability.

The compounds of the invention may be used clinically to treat medical conditions where an increased localized adenosine concentration is beneficial. Accordingly, the invention is directed to the treatment of ischemic conditions such as stroke, as well as other conditions benefitted by enhanced adenosine levels, such as inflammation, arthritis, seizures, epilepsy and other neurological conditions. The compounds are also useful for treating pain, as muscle relaxants, and for inducing sleep.

The invention is also directed to prodrugs and pharmaceutically acceptable salts of the compounds described, and to pharmaceutical compositions suitable for different routes of drug administration and which comprise a therapeutically effective amount of a described compound admixed with a pharmacologically acceptable carrier.

Definitions

The following terms generally have the following meanings.

The term "aryl" refers to aromatic groups, which have at least one ring having a conjugated pi electron system, including for example carbocyclic aryl, heterocyclic aryl and biaryl groups, all of which may be optionally substituted. Carbocyclic aryl groups are groups wherein all the ring atoms on the aromatic ring are carbon atoms, such as phenyl. Also included are optionally substituted phenyl groups, being preferably phenyl or phenyl substituted by one to three substituents, preferably lower alkyl, hydroxy, lower alkoxy, lower alkanoyloxy, halogen, cyano, perhalo lower alkyl, lower acylamino, lower alkoxycarbonyl, amino, alkylamino, carboxamido, and sulfonamido.

Heterocyclic aryl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, pyrimidyl, pyrazinyl, imidazolyl, and the like, all optionally substituted.

Optionally substituted furanyl represents 2- or 3-furanyl or 2- or 3-furanyl preferably substituted by lower alkyl or halogen. Optionally substituted pyridyl represents 2-, 3- or 4-pyridyl or 2-, 3- or 4-pyridyl preferably substituted by lower alkyl or halogen. Optionally substituted thienyl represents 2- or 3-thienyl, or 2- or 3-thienyl preferably substituted by lower alkyl or halogen.

The term "biaryl" represents phenyl substituted by carbocyclic aryl or heterocyclic aryl as defined herein, ortho, meta or para to the point of attachment of the phenyl ring, advantageously para; biaryl is also represented as —$C_6H_4$—Ar where Ar is aryl.

The term "aralkyl" refers to an alkyl group substituted with an aryl group. Suitable aralkyl groups include benzyl, picolyl, and may be optionally substituted.

The term "lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b)"arylamino", and (c) "aralkylamino", respectively, refer to the groups -NRR' wherein respectively, (a) R is alkyl and R' is hydrogen, aryl or alkyl; (b) R is aryl and R' is hydrogen or aryl, and (c) R is aralkyl and R' is hydrogen or aralkyl.

The term "acylamino" refers to RC(O)NR'—.

The term "carbonyl" refers to —C(O)—.

The term "carboxamide" or "carboxamido" refers to —CONR$_2$ wherein each R is independently hydrogen, lower alkyl or lower aryl.

The term "alkyl" refers to saturated aliphatic groups including straight-chain, branched chain and cyclic groups.

The term "alkenyl" refers to unsaturated alkyl groups which contain at least one carbon-carbon double bond and includes straight-chain, branched and cyclic groups.

The term "alkynyl" refers to unsaturated alkyl groups which contain at least one carbon-carbon triple bond and includes straight-chain, branched and cyclic groups.

The term "mercapto" refers to .SH or a tautomeric form thereof.

The term "alkylene" refers to a divalent straight chain or branched chain saturated aliphatic radical.

The term "sulfonamido" means —SO$_2$NHR where R is hydrogen or lower alkyl.

The term "N-sulfonyl amine" means —NHSO$_2$R where R is fluoro, lower perfluoroalkyl or lower alkyl.

The term "N-acylated sulfonamide" refers to the group —SO$_2$NHCOR where R is lower alkyl or lower perfluoroalkyl.

The term "basic nitrogen" generally refers to the nitrogen atom of an alkyl amine and implies a compound whose conjugated acid in aqueous solution has a pKa in the range of 9 to 11.

The term "prodrug" refers to any compound that, when administered to a biological system generates the "drug" substance either as a result of spontaneous chemical reaction or by enzyme catalyzed or metabolic reaction. Reference is made to various prodrugs such as acyl esters, carbonates, and urethanes, included herein as examples. The groups illustrated are exemplary, not exhaustive and one skilled in the art could prepare other known varieties of prodrugs. Such prodrugs of the compounds of the invention, fall within the scope of the invention.

The term "pharmaceutically acceptable salt" includes salts of compounds described herein derived from the combination of a compound of this invention and an organic or inorganic acid. The compounds of the present invention are useful in both free base and salt form in practice the use of salt form amounts to use of base form; both forms are within the scope of the present invention.

The term treatment includes prophylatic or therapeutic administration of compounds of the invention, for the cure or amelioration of disease or symptoms associated with disease, and includes any benefit obtained or derived from the administration of the described compounds.

DETAILED DESCRIPTION OF THE INVENTION

The invention relates to adenosine kinase inhibitors of the general Formula I.

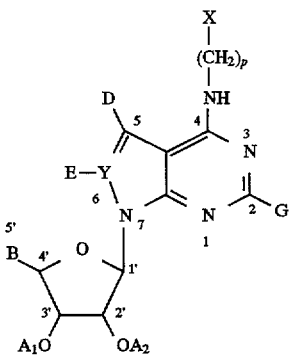

wherein:

$A_1$ and $A_2$ are each independently hydrogen, acyl, or taken together form a cyclic carbonate;

B is CH$_3$, alkenyl, or (CH$_2$)$_n$—B', where n is from 1 to 4 and B' is hydrogen, hydroxy, alkyl, alkoxy, amino, azido, or halogen;

D is halogen, aryl, aralkyl, alkynyl, haloalkyl, cyano, or carboxamido;

Y is carbon or nitrogen;

E is nothing when Y is nitrogen, and is hydrogen, halogen or alkyl when Y is carbon;

G is hydrogen or halogen;

p is from 0 to 3, preferably 0;

and X is a five or six member aryl ring, optionally substituted at any one or more positions by hydroxy, amino alkyl, alkoxy, per halo lower alkyl, sulfonamide, halogen, cyano, carboxamido, acylamino, NRR', or SR where R and R' are independently hydrogen or lower alkyl; and pharmaceutically acceptable salts thereof.

For convenience, the numbering scheme in Formula I is given for pyrrolo pyrimidine compounds (Y=C). It will be understood that the nomenclature and numbering scheme is different for the pyrazolo pyrimidine (Y=N) embodiments of the invention.

These compounds are potent adenosine kinase inhibitors, are superior in oral availability, and are suitably non-toxic.

Preferably, X is a six member ring (phenyl), the most preferred substitution is at the para position, and the most preferred substituent is halogen (e.g., fluorine). In theory, substitution of the ring structure as described, particularly at the para position of the phenylamino group (i.e. 4N-4-substituted phenylamino), blocks certain oxidation or glucoronidation sites, which in turn increases the half-life of the compound by reducing the rate of in vivo elimination after oral administration. The result is a more effective and longer-lasting compound when administered orally.

Also preferred are embodiments where $A_1$ and $A_2$ are hydrogen; and B is CH$_2$OH, or most preferably is CH$_3$. D is preferably aryl, and most preferably is phenyl or substituted phenyl. E is nothing when Y is nitrogen, and is preferably hydrogen when Y is carbon. G is also preferably hydrogen. Thus, preferred compounds can be represented by Formula 2:

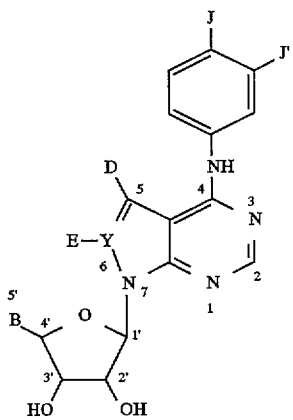

Formula 2 wherein
B is CH₂OH, or most preferably CH₃;
D is as defined in Formula I, or preferably is aryl, phenyl, or substituted phenyl;
E is halogen, alkyl, or most preferably hydrogen;
Y is carbon or nitrogen, preferably carbon;
and J and J' are independently halogen, preferably fluorine.

In another embodiment, preferred compounds are those of Formula 3.

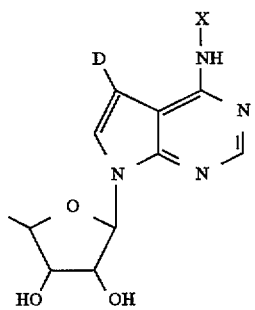

Formula 3 where D and X are each independently a substituted phenyl, such as

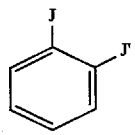

where J and J' are each independently halogen or cyano, preferably fluorine.

Prodrugs of the compounds of the present invention are included in the scope of this application. Such prodrugs may be prepared by esterification of the hydroxyl groups on the sugar moiety. Specially preferred will be the ester derivatives that improve water solubility or oral bioavailability.

Further, the compounds of the present invention contain asymmetric carbon atoms and hence can exist as stereoisomers, both enantiomers and diastereomers. The individual preferred stereoisomers and mixtures thereof are considered to fall within the scope of the present invention. The compounds described by Formula 1 may contain a 5-modified 1-β-D-ribofuranosyl group and that isomer comprises a particularly preferred diastereomeric and enantiomeric form for compounds of the present invention. It is also evident that in addition to the sugar moiety, additional asymmetric carbons may be present in compounds of the present invention, being present in moieties $A_1$, $A_2$ or B, or in the substituted heterocyclic pyrrolo[2,3-d]pyrimidine or pyrazolo[3,4-d]pyrimidine ring. In this event, both of the resulting diastereomers are considered to fall within the scope of the present invention.

SYNTHESIS OF ADENOSINE KINASE INHIBITORS

The compounds of the invention can be made by several reaction schemes, and for convenience can be grouped as pyrrolo or pyrazolo pyrimidines. Exemplary synthetic routes are given below.

SYNTHESIS OF PYRROLO PYRIMIDINES

EXAMPLE 1

PREFERRED PREPARATION OF PYRROLO PYRIMIDINES

Phenylated compounds of the invention can be made according to Scheme 1, below. A heterocycle, 5-aryl-4-arylaminopyrrolo[2,3-d]pyrimidine (6) is made by condensing a substituted phenacyl chloride or bromide (1) with potassium phthalimide (2) in a solvent such as N,N-dimethylformamide or acetonitrile at ambient temperature to obtain the phenacylphthalimide (3). This is further condensed with malononitrile in the presence of sodium methoxide to provide the desired 2-amino-3-cyano-4-phenylpyrrole (4). Refluxing (4) with triethylorthoformate provides the intermediate (5) which upon condensation with substituted anilines yields the desired heterocycle (6).

SCHEME 1

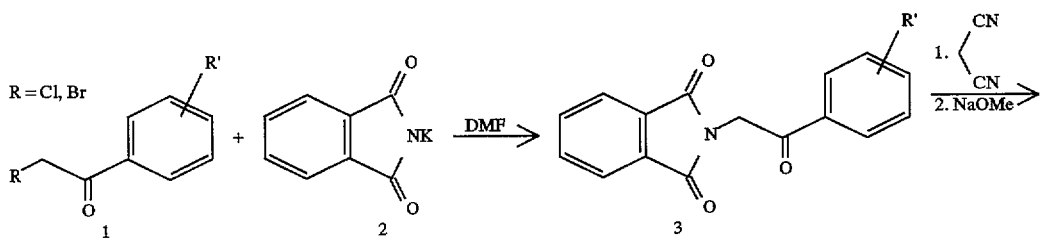

-continued
SCHEME 1

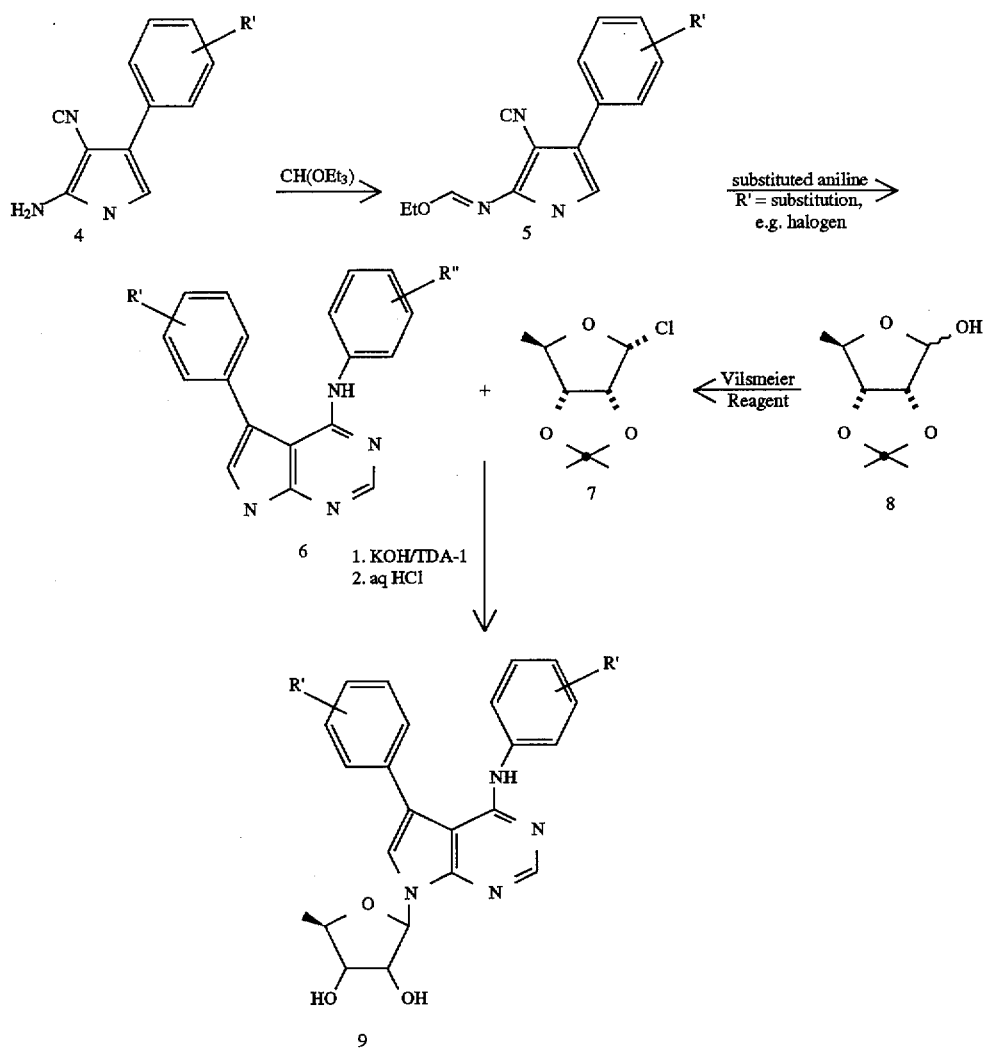

Desired 5-substituted-5-deoxy ribose analogs are prepared by tosylation of a suitably protected ribose, displacing the tosylate with an appropriate nucleophile, such as hydride or azide, and subsequent manipulation of the protecting groups. Snyder, J.; Serianni, A.; *Carbohydrate Research*, 163:169 (1987). The sugar, 1-alpha-chloro-5-deoxy-2,3-isopropylidene-D-ribofuranose (7) used in this process is made by reacting the corresponding sugar (8) with Viismeier reagent (DMF and oxalylchloride) at 0 C. It is further condensed with the heterocycle (6) in the presence of KOH and a phase transfer catalyst such as TDA-1 at ambient temperature. Rosemeyer H., and Seela, F, *Helvetica Chimica Acta*, 71:1573 (1988). The resulting protected nucleoside is subjected to deprotection under acidic conditions to obtain compound (9).

The following compounds were made by this procedure.
1) 4-N-(4-fluorophenyl)amino-5-phenyl-7-(5-deoxy-1-β-D-ribofuranosyl)pyrrolo(2,3-d)pyrimidine.
2) 4-N-(4-fluorophenyl)amino-5-(4-fluorophenyl)-7-(5-deoxy-1-β-D-ribofuranosyl)pyrrolo[2,3-d]pyrimidine.
3) 4-N-(4-chlorophenyl)amino-5-phenyl-7-(5-deoxy-1-β-D-ribofuranosyl)pyrrolo[2,3-d]pyrimidine.
4) 4-phenylamino-5-phenyl-7-(5-deoxy-1-β-D-ribofuranosyl)pyrrolo[2,3-d]pyrimidine.

The following compounds can also be synthesized in this way.
5) 4-N-(4-bromophenyl)amino-5-(phenyl)-7-(5-deoxy-1-β-D-ribofuranosyl)pyrrolo[2,3-d]pyrimidine.
6) 4-N-(3,4-dichlorophenyl)amino-5-(phenyl)-7-(5-deoxy-1-β-D-ribofuranosyl)pyrrolo[2,3-d]pyrimidine.
7) 4-N-(3,5-dichlorophenyl)amino-5-(phenyl)-7-(5-deoxy-1-β-D-ribofuranosyl)pyrrolo[2,3-d]pyrimidine.
8) 4-N-(3-chloro-4-fluorophenyl)amino-5-(phenyl)-7-(5-deoxy-1-β-D-ribofuranosyl)pyrrolo[2,3-d]pyrimidine.
9) 4-N-(4-fluorophenyl)amino-5-(4-chlorophenyl)-7-(5-deoxy-1-β-D-ribofuranosyl)pyrrolo[2,3-d]pyrimidine.
10) 4-N-(3,5-difluorophenyl)amino-5-phenyl-7-(5-deoxy-1-β-D-ribofuranosyl)pyrrolo[2,3-d]pyrimidine.
11) 4-N-(3,4-difluorophenyl)amino-5-phenyl-7-(5-deoxy-1-β-D-ribofuranosyl)pyrrolo[2,3-d]pyrimidine.
12) 4-N-(4-chlorophenyl)amino-5-(4-chlorophenyl)-7-(5-deoxy-1-β-D-ribofuranosyl) pyrrolo[2,3-d]pyrimidine.

Examples according to this reaction scheme follow.

EXAMPLE 2

DIARYL PYRROLOPYRIMIDINE NUCLEOSIDES

A. 2-Amino-3-cyano-4-phenylpyrrole, (4).

To a solution of phenacyl chloride (1) (500 g, 3.23M) in dry N,N-dimethylformamide (600 mL) was added potassium phthalimide, 2 (600 g, 3.23M) in small portions. The resulting mixture was stirred at ambient temperature overnight. To this was added malononitrile (256 g, 3.88M) in one lot followed by a 25 wt % solution of sodium methoxide in methanol (744 mL, 3.2 mol). The resulting mixture was stirred at room temperature overnight. Ice-water (10.0 L) was added to the reaction mixture and stirring was continued at room temperature overnight. The precipitate formed was collected by filtration and washed with cold water (4.0 L). The off-white solid was stirred in toluene (3.0 L) and filtered. The solid was washed with toluene (300 mL) and dried under vacuum at 60 C. overnight. Yield 298.56 g. m.p. 172–174 C.

B. 5-Phenyl-4-(4-fluorophenyl)aminopyrrolo[2,3-d]pyrimidine, (6)

A mixture of compound (4) (296.0 g, 1.62 mol) and triethylorthoformate (3.2 L) was refluxed for 1 h. The triethylorthoformate was distilled off under reduced pressure until the pot temperature reached 88 C. To the cooled reaction mixture hexane (3.0 L) was added with vigorous stirring. The contents of the vessel were cooled to 0 C. and the off-white solid formed was collected by filtration and washed with hexane (2×500 mL) and dried under suction. Final drying was done in a high vacuum oven. Yield of the 2-ethoxymethyleneimino-3-cyano-4-phenylpyrrole (5) was 323.0 g (83%). m.p. 98–100 C.

The above material (100 g, 0.42 mol) was dissolved in 1,2-dichlorobenzene. 4-Fluoroaniline (60 mL, 0.62 mol) was added and the reaction mixture was heated to 125 C. for 1 h. An additional 985 mL of 1,2-dichlorobenzene was added and the reaction temperature was raised to 140 C. for 3 h. Upon cooling to 0 C. the title compound precipitated as a yellow solid which was collected by filtration and dried under vacuum. Yield was 66.0 g. of the title compound, m.p. 215–218 C.

C. 5-(4-Fluorophenyl)-4-N-(4-fluorophenyl)aminopyrrolo[2,3-d]pyrimidine

This compound was made by a route similar to Examples 2A and 2B. Here, the phenacyl chloride was replaced with 4-fluorophenacyl chloride. m.p. 245–248 C.

D. 5-phenyl-4-N-(4-chlorophenyl)aminopyrrolo[2,3-d]pyrimidine

This compound was made by a route similar to Example 2B. Here, the 4-fluoroaniline was replaced with 4-chloroaniline. m.p. 233–236 C.

E. 5-phenyl-4-N-phenylaminopyrrolo[2,3-d]pyrimidine

This compound was made by a route similar to Example 2B. Here, the 4-fluoroaniline aniline was replaced with aniline. m.p. 210–215 C.

F. 6-Bromo-5-phenyl-4-N-phenylaminopyrrolo[2,3-d]pyrimidine 5-phenyl-4-phenylaminopyrrolo[2,3-d]pyrimidine (1.5 g) was dissolved in dry DMF (25.0 mL) and treated with N-bromosuccinamide (1.8 g). Stirring was continued for 18 h and the solvent was evaporated. The residue was treated with water (10 mL) and the solid was collected by filtration. Crystallization from boiling ethanol provided the title compound. Yield 1.6 g. m.p. 240–249 C. Rf=0.6, SiO$_2$, 4:1 Ethyl acetate:hexane.

G. 6-Bromo-4-N-(4-fluorophenyl)amino-4-phenylpyrrolo[2,3-d]pyrimidine

The compound was made by a procedure similar to the one above. m.p. >250 C. Rf=0.6, SiO$_2$, 4:1 Ethyl acetate:hexane.

EXAMPLE 3

GLYCOSYLATION OF PYRROLOPYRIMIDINE HETEROCYCLES

The procedure described here for the glycosylation of 4-N-(4-fluorophenyl)amino-5-phenylpyrrolo[2,3-d]pyrimidine exemplifies a general method of glycosylation for the pyrrolopyrimidine heterocycles.

Into a one liter three neck flask fitted with a thermometer, an addition funnel and a mechanical stirrer, was taken a mixture of toluene (290 mL), acetonitrile (100 mL), and N,N-dimethylformamide (100mL). Oxalyl chloride (28.6 mL, 328 mmol) was added dropwise to the reaction mixture through the addition funnel. After the addition was completed the mixture was stirred at room temperature for 15 rain and the cooled to −12 C. A solution of 5-deoxy-2,3-isopropylidene-D-ribofuranose (57.2 g, 328 mmol) in toluene (58 mL) was cooled to −12 C. and added to the reaction mixture through the addition funnel at such a rate that the reaction temperature remained at −12 C. After the addition was completed the reaction mixture was stirred at −12 C. for 20 min. The chloro sugar solution thus formed was canulated into an ice-cooled solution of triethylamine (58 mL) in toluene (145 mL). After stirring for 15 min the reaction mixture was filtered and the solid was washed with toluene (2×50 ml) and the filtrate was kept in an ice bath.

A 2 liter three neck flask equipped with a mechanical stirrer and an addition funnel was charged with the heterocycle, e.g. compound (6) (50 g, 164 mmol), freshly powdered KOH (21.7 g, 328 mmol) and toluene (430 mL). To the well stirred mixture was added TDA-1 catalyst (53.0 mL) and stirring was continued for 15 min. The above solution of the chloro sugar was added, and the mixture was stirred over-night at room temperature. The dark reaction mixture was washed with water (500 mL), brine (200 mL) and the organic phase was concentrated in vacuum to give a dark oil. This product was dissolved in methanol (450 mL) and the resulting solution was diluted with 200 mL of 1 N HCl. The reaction temperature was raised to 64–65 C. for 6.5 h under vigorous stirring and then cooled to 25 C. The acid was neutralized to pH ~7-8 using NaHCO$_3$ solution. The reaction mixture was diluted with water (200 mL) and the precipitate that formed was collected by filtration, washed with water (2×100 mL) and dried under suction. The wet solid was crystallized from boiling ethanol. Yield 41.17 g (59.6 %). m.p. 187–189 C.

EXAMPLE 4

ALTERNATIVE PREPARATION OF PYRROLO PYRIMIDINES

Alternatively compounds of the invention can be made according to the procedure described in Browne et al. Ser. No. 08/812,916. Briefly, reaction of 4-chloro-5-iodo-7-(1-β-D-5-deoxyribofuranosyl)pyrrolo[2,3-d]pyrimidine with an amine in refluxing ethanol leads to the formation of a 4-(N-substituted) amino-5-iodo-7-(1-β-D-5-deoxyribofuranosyl)pyrrolo[2,3-d]pyrimidine. This iodo compound is treated with an aryl boronic acid in the presence of a palladium catalyst to generate the targeted 4-(N- substituted)amino-5-aryl-7-(1-β-D-5-deoxyribofuranosyl) pyrrolo[2,3-d]pyrimidine, which is purified by chromatography and/or recrystallization from a suitable solvent. Thus, a halogenated nucleoside or the corresponding base was heated with an arylboronic acid and a palladium-phosphine catalyst such as palladium tetrakis (triphenylphosphine) to prepare the analogous arylated compound by displacement of halogen. Various 5-arylated pyrrolo[2,3-d]pyrimidines also can be prepared using arylstannyl compounds in place of the arylboronic acids. Flynn, B.; Macolino, B.; Crisp, G. *Nucleosides & Nucleosides*, 10:763 (1991).

EXAMPLE 5

PREPARATION OF REPRESENTATIVE COMPOUNDS

A. Preparation of 4-N-(4-chlorophenyl)amino-5-iodo-7-(5-deoxy-1-β-D-5-ribofuranosyl)pyrrolo[2,3-d]pyrimidine.

A mixture of 4-chloro-5-iodo-7-(5-deoxy-1-β-D-ribofuranosyl)pyrrolo[2,3-d]pyrimidine (190 mg) and 180 mg of 4-chloroaniline in 5 mL of ethanol was heated in a sealed bottle at 90 C. for 48 h and at 135 C. for an additional 12h. The bottle was cooled in an ice bath, opened and the precipitated solid filtered. Recrystallization from ethanol-ether afforded 135 mg of the title compound. m.p. 234–235 C.

B. Preparation of 4-N-(4-chlorophenyl)amino-5-phenyl-7-(5-deoxy-1-β-D-ribofuranosyl)pyrrolo[2,3-d]pyrimidine.

In a round bottom flask were placed 40 mg of 4-(4-chlorophenylamino)-5-iodo-7-(5-deoxy-1-β-D-ribofuranosyl)pyrrolo[2,3-d]pyrimidine, 50 mg of 4-chlorophenyl boronic acid, 10 mg of Pd (PPh$_3$)$_4$ and 4.0 mL of diglyme. To this was added 1.0 mL of ethanol, 0.4 mL of a saturated aqueous solution of sodium carbonate and heated at 100 C. for 2.5 h. After filtration of the mixture through a celite pad and removal of the aqueous layer, the organic phase was evaporated under reduced pressure and chromatographed on silica gel eluting with 30:1 CH$_2$Cl$_2$:CH$_3$OH. The product obtained was crystallized from ethanol to afford 35 mg of the title compound as a tan solid, m.p. 176–178 C.

C. Selective Phenylation of Substituted Pyrrolo Pyrimidines.

Phenylation of 4-N-(4-fluorophenyl)amino-5-iodo-7-(5-deoxy-2,3-isopropylidene-1-β-D-ribofuranosyl)pyrrelo[2,3-d]pyrimidine can be achieved according to the following protocol.

A mixture of 4-N-(4-fluorophenyl)amino-5-iodo-7-(5-deoxy-2,3-isopropylidine-1-β-D-ribofuranosyl)pyrrolo[2,3-d]pyrimidine (509 mg, 1 mmol), diglyme (20 mL) phenylboronic acid (608 mg, 4 mmol), tetrakistriphenyphosphine palladium catalyst (130 mg) and saturated sodium carbonate solution (3.0 mL) and ethanol (1 mL) was refluxed under nitrogen atmosphere for 4 hours. Completion of the reaction was evidenced by RPTLC using 3:1 methanol:water as eluent. The reaction mixture was filtered and the residue was washed with ethanol (1×10 mL). The filtrate was concentrated under reduced pressure and the residue was chromatographed on SiO$_2$ using 3:1 hexane:ethyl acetate as eluting solvent. Appropriate fractions were combined and evaporated to obtain the desired product as a glassy material. Yield 450 mg. The product was dissolved in 70% TFA (20 mL) and stirred at room temperature for 1.5 hours. Volatiles were evaporated and the residue was coevaporated with water (3×20 mL) and once with ethanol (1×10 mL). The residue was suspended in water (10 mL) and treated with NaHCO$_3$ solution (3 mL). The precipitate was collected by filtration, washed with water and dried, and the product was crystallized from boiling ethanol. Yield 310 mg. m.p.187–189 C.

The methods of Examples 1–5, with modifications that will be apparent, were used to synthesize the following compounds.

2) 4-N-(4-fluorophenyl)amino-5-(4-fluorophenyl)-7-(5-deoxy-1-β-D-ribofuranosyl)pyrrolo[2,3-d]pyrimidine.

12) 4-N-(4-chlorophenyl)amino-5-(4-chlorophenyl)-7-(5-deoxy-1-β-D-ribofuranosyl pyrrolo[2,3-d] pyrimidine, m.p. 199–201

13) 4-(N-4-methoxyphenyl)amino-5-phenyl-7-(5-deoxy-1-β-D-ribofuranosyl) pyrrolo[2,3-d]pyrimidine; m.p. 162–165

14) 4-phenylamino-5-phenyl-7-(5-deoxy-1-β-D-ribofuranosyl)pyrrolo[2,3-d]pyrimidine

15) 4-N-phenylamino-5-(3-chlorophenyl)-7-(5-deoxy-1-β-D-ribofuranosyl) pyrrolo[2,3-d]pyrimidine, m.p. 223–225

16) 4-N-phenylamino-5-(4-methylphenyl)-7-(5-deoxy-1-β-D-ribofuranosyl) pyrrolo[2,3-d]pyrimidine, m.p. 215–217

17) 4-N-(3-chlorophenyl)amino-5-phenyl-7-(5-deoxy-1-β-D-ribofuranosyl) pyrrolo[2,3-d]pyrimidine, m.p. 224–226

18) 4-N-(3-methylphenyl)amino-5-phenyl-7-(5-deoxy-1-β-D-ribofuranosyl) pyrrolo[2,3-d]pyrimidine, m.p. 207–209

19) 4-N-(3-fluorophenyl)amino-5-phenyl-7-(5-deoxy-1-β-D-ribofuranosyl) pyrrolo[2,3-d]pyrimidine, m.p. 223–225 b 20) 4-N-(4-hydroxyphenyl)amino-5-phenyl-7-(5-deoxy-1-β-D-ribofuranosyl) pyrrolo[2,3-d]pyrimidine, m.p. 188–191

21) 4-N-(4-cyanophenyl)amino-5-phenyl-7-(5-deoxy-1-β-D-ribofuranosyl) pyrrolo[2,3-d]pyrimidine, m.p. 194–196

22) 4-N-(4-trifluoromethylphenyl)amino-5-phenyl-7-(5-deoxy-1-β-D-ribofuranosyl) pyrrolo[2,3-d]pyrimidine, m.p. 195–197

23) 4-N-(4-methylphenyl)amino-5-phenyl-7-(5-deoxy-1-β-D-ribofuranosyl)pyrrolo[2,3-d]pyrimidine, m.p. 180–182

24) 4-N-phenylamino-5-(4-fluorophenyl)-7-(5-deoxy-1-β-D-ribofuranosyl) pyrrolo[2,3-d]pyrimidine, m.p. 225–227

25) 4-N-(4-fluorophenyl)amino-5-(4-methoxyphenyl)-7-(5-deoxy-1-β-D-ribofuranosyl)pyrrolo[2,3-d] pyrimidine, m.p. 192–194.

26) 4-N-(4-cyanophenyl)amino-5-(4-fluorophenyl)-7-(5-deoxy-1-β-D-ribofuranosyl) pyrrolo[2,3-d] pyrimidine, m.p. 123–126

11) 4-N-(3,4-difluorophenyl)amino-5-phenyl-7-(5-deoxy-1-β-D-ribofuranosyl)pyrrolo[2,3-d]pyrimidine, m.p. 225–226

10) 4-N-(3,5-difluorophenyl)amino-5-phenyl-7-(5-deoxy-1-β-D-ribofuranosyl) pyrrolo[2,3-d]pyrimidine, m.p. 265–267

27) 4-N-(4-cyanophenyl)amino-5-(4-methoxyphenyl)-7-(5-deoxy-1-β-D-ribofuranosyl)pyrrolo[2,3-d] pyrimidine, m.p. 207–210

28) 4-N-(4-ethoxyphenyl)amino-5-phenyl-7-(5-deoxy-1-β-D-ribofuranosyl) pyrrolo[2,3-d]pyrimidine, m.p. 173–175

29) 4-N-(4-ethylphenyl)amino-5-phenyl-7-(5-deoxy-1-β-D-ribofuranosyl) pyrrolo[2,3-d]pyrimidine, m.p. 154–156

30) 4-N-(4-fluorophenyl)amino-5-(3-nitrophenyl)-7-(5-deoxy-1-β-D-ribofuranosyl) pyrrolo[2,3-d]pyrimidine, m.p. 188–190

31) 4-N-(4-carbamoylphenyl)amino-5-(4-methoxyphenyl)-7-(5-deoxy-1-β-D-ribofuranosyl) pyrrolo[2,3-d]pyrimidine, m.p. 223–224

32) 4-N-(4-N-acetylaminophenyl)amino-5-phenyl-7-(5-deoxy-1-β-D-ribofuranosyl) pyrrolo[2,3-d]pyrimidine, m.p. 223–224

33) 4-N-(4-methoxyphenyl)amino-5-(2-furyl)-7-(5-deoxy-1-β-D-ribofuranosyl) pyrrolo[2,3-d]pyrimidine, m.p. 222–224

34) 4-N-(4-sulfonamidophenyl)amino-5-phenyl-7-(5-deoxy-1-β-D-ribofuranosyl) pyrrolo[2,3-d]pyrimidine, m.p. 174–177

35) 4-N-phenylamino-5-phenyl-7-(5-deoxy-5-azido-β-D-ribofuranosyl)pyrrolopyrimidine

36) 4-N-phenylamino-5-phenyl-7-(5-deoxy-5-amino-β-D-ribofuranosyl)pyrrolopyrimidine

37) 4-N-phenylamino-5-phenyl-7-(1-β-D-ribofuranosyl)pyrrolo[2,3-d]pyrimidine

38) 4-N-benzylamino-5-phenyl-7-(5-deoxy-1-β-D-ribofuranosyl)pyrrolo[2,3-d]pyrimidine

39) 4-N-phenylamino-5-(4-chlorophenyl)-7-(5-deoxy-1-β-D-ribofuranosyl) pyrrolo[2,3-d]pyrimidine

40) 4-N-(4-methylthiophenyl)amino-5-phenyl-7-(5-deoxy-1-β-D-ribofuranosyl) pyrrolo[2,3-d]pyrimidine

41) 6-bromo-7-(5-deoxy-1-β-D-ribofuranosyl)-4-N-(4-fluorophenyl)amino-5-phenylpyrrolo[2,3-d]pyrimidine

42) 6-bromo-7-(5-deoxy-1-β-D-ribofuranosyl)-5-phenyl-4-N-phenylaminopyrrolo[2,3-d]pyrimidine

43) 4-N-(4-aminophenyl)amino-5-phenyl-7-(5-deoxy-1-β-D-ribofuranosyl)pyrrolo[2,3-d]pyrimidine The following compounds can be made as described.

44) 4-N-(4-fluorophenyl)amino-5-(4-fluorophenyl)-7-(1-β-D-ribofuranosyl)pyrrolo[2,3-d]pyrimidine

45) 4-N-(4-fluorophenyl)amino-5-phenyl-7-(5-deoxy-5-chloro-1-β-D-ribofuranosyl)pyrrolo[2,3-d]pyrimidine

46) 4-N-(4-fluorophenyl)amino-5-phenyl-7-(1-β-D-ribofuranosyl)pyrrolo[2,3-d]pyrimidine

47) 4-N-(4-fluorophenyl)amino-5-phenyl-7-(5-deoxy-5-azido-1-β-D-ribofuranosyl)pyrrolo[2,3-d]pyrimidine

48) 4-N-(4-fluorophenyl)amino-5-(4-fluorophenyl)-7-(5-deoxy-5-azido-1-β-D-ribofuranosyl)pyrrolo[2,3-d]pyrimidine

49) 4-N-(2-fluorophenyl)amino-5-phenyl-7-(5-deoxy-1-β-D-ribofuranosyl)pyrrolo[2,3-d]pyrimidine

50) 4-N-(4-fluorophenyl)amino-5-(4-cyanophenyl)-7-(5-deoxy-1-β-D-ribofuranosyl)pyrrolo[2,3-d]pyrimidine

51) 4-N-(4-fluorophenyl)amino-5-(4-carboxamidophenyl)-7-(5-deoxy-1-β-D-ribofuranosyl)pyrrolo[2,3-d]pyrimidine

52) 4-N-(4-fluorophenyl)amino-5-(4-trifluoromethylphenyl)-7-(5-deoxy-1-β-D-ribofuranosyl)pyrrolo[2,3-d]pyrimidine

53) 4-N-(4-fluorophenyl)amino-5-(4-sulfonylamidophenyl)-7-(5-deoxy-1-β-D-ribofuranosyl)pyrrolo[2,3-d]pyrimidine

54) 4-N-(4-fluorophenyl)amino-5-(4-bromophenyl)-7-(5-deoxy-1-β-D-ribofuranosyl)pyrrolo[2,3-d]pyrimidine

55) 4-N-(4-fluorophenyl)amino-5-(4-hydroxyphenyl)-7-(5-deoxy-1-β-D-ribofuranosyl)pyrrolo[2,3-d]pyrimidine

56) 4-N-(4-fluorophenyl)amino-5-(3-chloro-4-fluorophenyl)-7-(5-deoxy-1-β-D-ribofuranosyl)pyrrolo[2,3-d]pyrimidine

57) 4-N-(4-fluorophenyl)amino-5-(4-methylphenyl)-7-(5-deoxy-1-β-D-ribofuranosyl)pyrrolo[2,3-d]pyrimidine

58) 4-N-(4-fluorophenyl)amino-5-4-phenyl-6-bromo-7-(5-deoxy-1-β-D-ribofuranosyl)pyrrolo[2,3-d]pyrimidine

59) 4-N-(4-fluorophenyl)amino-5-(4-phenyl)-6-methyl-7-(5-deoxy-1-β-D-ribofuranosyl)pyrrolo[2,3-d]pyrimidine

60) 4-N-(4-fluorophenyl)amino-5-(3-fluorophenyl)-7-(5-deoxy-1-β-D-ribofuranosyl)pyrrolo[2,3-d]pyrimidine

61) 4-N-(4-fluorophenyl)amino-5-(2-oxazolyl)-7-(5-deoxy-1-β-D-ribofuranosyl)pyrrolo[2,3-d]pyrimidine

62) 4-N-(4-fluorophenyl)amino-5-(2-thienyl)-7-(5-deoxy-1-β-D-ribofuranosyl)pyrrolo[2,3-d]pyrimidine

63) 4-N-(4-fluorophenyl)amino-5-(4-methylphenyl)-7-(5-deoxy-1-β-D-ribofuranosyl)pyrrolo[2,3-d]pyrimidine

64) 4-N-(4-fluorophenyl)amino-5-(4-ethylphenyl)-7-(5-deoxy-1-β-D-ribofuranosyl)pyrrolo[2,3-d]pyrimidine

65) 4-N-(4-fluorophenyl)amino-5-(4-carboxymethyloxyphenyl)-7-(5-deoxy-1-β-D-ribofuranosyl)pyrrolo[2,3-d]pyrimidine

66) 4-N-(4-fluorophenyl)amino-5-(4-thiazolyl)-7-(5-deoxy-1-β-D-ribofuranosyl)pyrrolo[2,3-d]pyrimidine

67) 4-N-(4-chlorophenyl)amino-5-phenyl-7-(1-β-D-ribofuranosyl)pyrrolo[2,3-d]pyrimidine

68) 4-N-(4-fluorophenyl)amino-5-(4-fluorophenyl)-7-(5-deoxy-1-β-D-ribofuranosyl)pyrrolo[2,3-d]pyrimidine

69) 4-N-(4-chlorophenyl)amino-5-(4-fluorophenyl)-7-(5-deoxy-1-β-D-ribofuranosyl)pyrrolo[2,3-d]pyrimidine

70) 4-N-(3,4-dichlorophenyl)amino-5-phenyl-7-(5-deoxy-1-β-D-ribofuranosyl)pyrrolo[2,3-d]pyrimidine

71) 4-N-(3-fluorophenyl)amino-5-phenyl-7-(5-deoxy-1-β-D-ribofuranosyl)pyrrolo[2,3-d]pyrimidine

72) 4-N-(3-cyanophenyl)amino-5-phenyl-7-(5-deoxy-1-β-D-ribofuranosyl)pyrrolo[2,3-d]pyrimidine

73) 4-N-(4-carboxamidophenyl)amino-5-phenyl-7-(5-deoxy-1-β-D-ribofuranosyl)pyrrolo[2,3-d]pyrimidine

74) 4-N-(phenethyl)amino-5-phenyl-7-(5-deoxy-1-β-D-ribofuranosyl)pyrrolo[2,3-d]pyrimidine

75) 4-N-(4-N-methylcarboxamidophenyl)amino-5-phenyl-7-(5-deoxy-1-β-D-ribofuranosyl)pyrrolo[2,3-d]pyrimidine

76) 4-N-(4-N-ethylcarboxamidophenyl)amino-5-phenyl-7-(5-deoxy-1-β-D-ribofuranosyl)pyrrolo[2,3-d]pyrimidine

77) 4-N-(4-N,N-dimethylcarboxamidophenyl)amino-5-phenyl-7-(5-deoxy-1-β-D-ribofuranosyl)pyrrolo[2,3-d]pyrimidine

78) 4-N-(4-N,N-diethylcarboxamidophenyl)amino-5-phenyl-7-(5-deoxy-1-β-D-ribofuranosyl)pyrrolo[2,3-d]pyrimidine

79) 4-N-(3-sulfonylamidophenyl)amino-5-phenyl-7-(5-deoxy-1-β-D-ribofuranosyl)pyrrolo[2,3-d]pyrimidine

80) 4-N-(3-trifluoromethylphenyl)amino-5-phenyl-7-(5-deoxy-1-β-D-ribofuranosyl)pyrrolo[2,3-d]pyrimidine

81) 4-N-(3-fluoro-4-chlorophenyl)amino-5-phenyl-7-(5-deoxy-1-β-D-ribofuranosyl)pyrrolo[2,3-d]pyrimidine

82) 4-N-(4-(2-methylethyl)phenyl)amino-5-phenyl-7-(5-deoxy-1-β-D-ribofuranosyl)pyrrolo[2,3-d]pyrimidine

83) 4-N-(4-fluorophenyl)amino-5-(benzyl)-7-(5-deoxy-1-β-D-ribofuranosyl)pyrrolo[2,3-d]pyrimidine

84) 4-N-(3-cyanophenyl)amino-5-(4-methoxyphenyl)-7-(5-deoxy-1-β-D-ribofuranosyl)pyrrolo[2,3-d]pyrimidine

85) 4-N-(3-carboxamidophenyl)amino-5-(4-methoxyphenyl)-7-(5-deoxy-1-β-D-ribofuranosyl)pyrrolo[2,3-d]pyrimidine

EXAMPLE 6

6-SUBSTITUTED COMPOUNDS

The 6-halosubstituted pyrrolo[2,3-d]pyrimidine nucleosides of the invention can be prepared by halogenation of the base, as described in Example 2F (preparation of 6-bromo-5-phenyl-4-N-phenylaminopyrrolo[2,3-d]pyrimidine) followed by ribosylation and deprotection as described in Example 3. It will be apparent that other halogenated analogs can be prepared in a similar fashion.

The preparation of 6-alkyl substituted pyrrolo [2,3-d] pyrimidines generally follows the sequence outlined in Example 1, except that the pheacyl chloride has an appropriate alkyl substitutent at the aliphatic carbon alpha to the carbonyl group.

SYNTHESIS OF PYRAZOLO PYRIMIDINES

EXAMPLE 7

PREPARATION OF PYRAZOLO PYRIMIDINES

Still another aspect of this invention is the preparation of 5'-modified pyrazolo[3,4-d]pyrimidine ribosides. Accordingly, a substituted pyrazolo[3,4-d]pyrimidine is ribosylated with an esterified 5-deoxy- or 5-deoxy-5-azido-ribofuranoside analog in the presence of a Lewis acid such as boron trifluoride. Browne et al., Ser. No. 08/812,916; Cottam, et al., *J. Med. Chem.*, 27:1120 (1984).

The 5-substituted sugar is prepared by esterification of the deblocked sugar. Suitable esters include the acetate, benzoate, toluate, anisoate and the like. The substituted pyrazolo[3,4-d]pyrimidine base may be prepared by a variety of known procedures which are apparent to practitioners. Another exemplary synthetic route follows.

One route comprises coupling an esterified ribose prepared as described above with a 3-substituted pyrazolo[3,4-d]pyrimidin-4-one. After ribosylation the pyrimidone riboside may be activated by chlorination with thionyl chloride/dimethyl-formamide or other reagents previously described and then reacted with ammonia or an amine to provide a variety of substituted 5'-modified N-4-substituted-aminopyrazolo[3,4-d]pyrimidine nucleosides.

Another route for preparation of substituted pyrazolo[3,4-d]pyrimidine nucleosides comprises coupling the esterified ribose with various substituted 4-amino or 4-substituted aminopyrazolo[3,4-d]pyrimidines, using procedure similar to those described for the pyrrolo pyrimidines. The resulting products are then further modified or deblocked to afford the desired compounds. For example, 3-phenyl-4-phenylaminopyrazolo[3,4-d]pyrimidine 5-modified ribosides are prepared from 3-phenyl-4-phenylaminopyrazolo[3,4-d]pyrimidine and various 5'-modified sugars.

In another aspect of the present invention, 3-halogenated pyrazolo[3,4 d]pyrimidine ribosides can be arylated using arylboronic acids and palladium catalysts as described for the pyrrolo[2,3-d]pyrimidines.

The required 3-iodopyrazolo[3,4-d]pyrimidone nucleosides are prepared by nonaqueous diazotization-iodination of the 3-amino compounds using a nitrite ester such as isoamyl nitrite and methylene iodide. Alternatively, 4-chloro or 4-amino pyrazolo[3,4-d]pyrimidine may be iodinated using N-iodosuccinimide in a solvent such as DMF and the resulting 5-iodo heterocycle is coupled to the sugar to obtain the desired 4-iodinated pyrazolo[3,4-d]pyrimidine nucleoside.

EXAMPLE 8

PREFERRED PREPARATION OF PYRAZOLO PYRIMIDINES

The general route for the synthesis of various 3-aryl-4-arylamino pyrazoloo[3,4-d]pyrimidine nucleosides is delineated in Scheme 2. Various 3-arylsubstituted 5-aminopyrazole-4-carbonitriles (10) were synthesized by a procedure analogous to the one reported in Kobayashi, *Chem. Pharm. Bull.* (Japan) 21, 941 (1973). These intermediates were further converted by a three step procedure to provide various 3-aryl-4-arylaminopyrazoloo[3,4-d]yrimidine bases (11) used for synthesis of final compounds. Cheng, C. C., Robins, R. K., J. Org. Chem., 21, 1240 (1966).

The carbohydrate moieties used in the current invention, e.g. 5-azido-5-deoxy-1,2,3-tri-O-acetyl-ribofuranose (15), where B=$CH_2N_3$ were synthesized as shown in Scheme 2. Treatment of (13) (Snyder, J.; Serianni, A.; *Carbohydrate Research*, 163:169 (1987)) with sodium azide in dry DMF at elevated temperatures provided the corresponding 5-azido ribofuranoside (14) which was subjected to removal of the protecting groups under acidic conditions and the resulting ribose was acetylated with acetic anhydride and pyridine to provide (15). 5-Deoxy-1,2,3-tri-O-acetyl-D-ribofuranose (16) used in the current invention was synthesized by subjecting (13) to LAH reduction to provide methyl 5-deoxy-2,3-isopropylidene-D-ribofuranose, followed by appropriate protecting group manipulations.

Coupling of heterocycles with the above ribofuranose moieties was conducted in boiling nitromethane using $BF_3$-etherate as a catalyst to obtain blocked nucleosides which upon deblocking with sodium methoxide in methanol provided the desired 5'-modified 3-aryl-4-arylaminopyrazolo[3,4-d]pyrimidine nucleosides of general structure (12). The 5'-azido analogs are then subjected to reduction with triphenyl-phosphine and pyridine to provide the corresponding 5'-amino analogs.

SCHEME 2

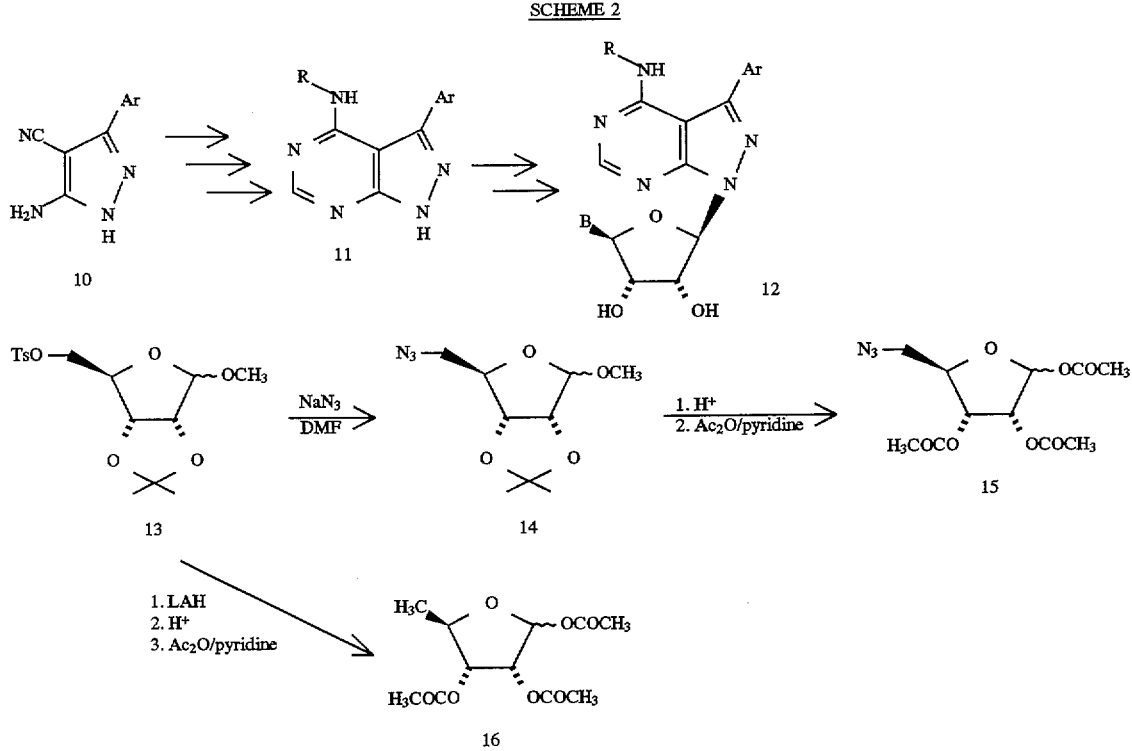

Alternatively, the azide function could be reduced by catalytic hydrogenation or by using other reagents such as propanethiol/acetic acid or sodium dithionite.

The following compounds were made.

86) 4-N-phenylamino-3-phenyl-1-(5'-deoxy-1-β-D-ribofuranosyl)pyrazolo[3,4-d]pyrimidine

87) 1-(5-azido-5-deoxy-1-β-D-ribofuranosyl)-3-phenyl-4-N-phenylaminopyrazolo[3,4-d]pyrimidine

88) 3-phenyl-4-N-phenylamino-1-(1-β-D-ribofuranosyl)pyrazolo[3,4-d]pyrimidine

89) 4-N-[(p-methoxyphenyl)amino]-3-phenyl-1-(5-deoxy-ribofuranosyl)pyrazolo[3,4-d]pyrimidine.

90) 1-(5-azido-5-deoxy-1-β-D-ribofuranosyl)-4-N-(4-methoxyphenylamino)-3-phenylpyrazolo[3,4-d]pyrimidine.

91) 4-N-(4-methoxyphenyl)amino-3-phenyl-1-(5-deoxyribofuranosyl)pyrazolopyrimidine

92) 1-(5-azido-5-deoxy-1-β-D-ribofuranosyl)4-N-(4-chlorophenyl)amino-3-phenylpyrazolo[3,4-d]pyrimidine.

93) 1-(5-azido-5-deoxy-1-β-D-ribofuranosyl)-3-(4-methylphenyl)-4-N-phenylaminopyrazolo[3,4-d]pyrimidine.

94) 1-(5-azido-5-deoxy-1-β-D-ribofuranosyl)-3-(4-methoxyphenyl)-4-N-phenylaminopyrazolo[3,4-d]pyrimidine.

95) 1-(5-azido-5-deoxy-1-β-D-ribofuranosyl)-4-N-(4-methoxyphenyl)amino-3-(4-methylphenyl)-pyrazolo[3,4-d]pyrimidine.

96) 1-(5-azido-5-deoxy-1-β-D-ribofuranosyl)-3-(4-chlorophenyl)-4-N-phenylaminopyrazolo[3,4-d]pyrimidine.

97) 1-(5-azido-5-deoxy-1-β-D-ribofuranosyl)-3-(2-thienyl)-4-(phenylamino)pyrazolo[3,4-d]pyrimidine.

The following exemplary compounds can be made by same procedure.

98) 1-(5-deoxy-1-β-D-ribofuranosyl)-3-(4-chlorophenyl)-4-N-(4-fluorophenylamino)pyrazolo[3,4-d]pyrimidine.

99) 1-(5-azido-5-deoxy-1-β-D-ribofuranosyl)-3-(4-fluorophenyl-4-N-phenylaminopyrazolo[3,4-d]pyrimidine.

100) 1-(5-azido-5-deoxy-1-β-D-ribofuranosyl)-3-(4-fluorophenyl)-4-N-(4-fluorophenylamino)pyrazolo[3,4-d]pyrimidine.

101) 1-(5-azido-5-deoxy-1-β-D-ribofuranosyl)-3-(4-fluorophenyl)-4-N-(cyanophenyl)aminopyrazolo[3,4-d]pyrimidine.

102) 1-(5-azido-5-deoxy-1-β-D-ribofuranosyl)-3-(4-fluorophenyl)-4-N-(carbamoylphenyl)aminopyrazolo[3,4-d]pyrimidine.

103) 1-(5-deoxy-1-β-D-ribofuranosyl)-3-phenyl-4-N-(fluorophenyl)aminopyrazolo[3,4-d]pyrimidine.

104) 1-(5-deoxy-1-β-D-ribofuranosyl)-3-(3,4-difluorophenyl)-4-N-(fluorophenyl)aminopyrazolo[3,4-d]pyrimidine.

105) 1-(5-deoxy-1-β-D-ribofuranosyl)-3-(3-chloro-4-fluorophenyl)-4-N-(4-fluorophenyl)aminopyrazolo[3,4-d]pyrimidine.

106) 1-(5-deoxy-1-β-D-ribofuranosyl)-3-(3,4-difluorophenyl)-4-N-(4-fluorophenyl)aminopyrazolo[3,4-d]pyrimidine.

107) 1-(5-deoxy-1-β-D-ribofuranosyl)-3-(4-fluorophenyl)-4-N-(4-fluorophenyl)aminopyrazolo[3,4-d]pyrimidine.

108) 1-(5-deoxy-1-β-D-ribofuranosyl)-3-(4-methoxyphenyl)-4-N-(4-fluorophenyl)aminopyrazolo[3,4-d]pyrimidine.

21

109) 1-(5-deoxy-1-β-D-ribofuranosyl)-3-(4-ethylphenyl)-4-N-(4-fluorophenyl)aminopyrazolo[3,4-d]pyrimidine.

110) 1-(5-deoxy-1-β-D-ribofuranosyl)-3-(3-oxazolyl)-4-N-(4-fluorophenyl)aminopyrazolo[3,4-d]pyrimidine.

111) 1-(5-deoxy-1-β-D-ribofuranosyl)-3-phenyl-4-N-(3-fluorophenyl)aminopyrazolo[3,4-d]pyrimidine.

112) 1-(5-deoxy-1-β-D-ribofuranosyl)-3-phenyl-4-N-(3-chlorophenyl)aminopyrazolo[3,4-d]pyrimidine.

113) 1-(5-deoxy-1-β-D-ribofuranosyl)-3-phenyl-4-N-(3,4-difluorophenyl)aminopyrazolo[3,4-d]pyrimidine.

114) 1-(5-deoxy-1-β-D-ribofuranosyl)-3-phenyl-4-N-(3-chloro-4-fluorophenyl)aminopyrazolo[3,4-d]pyrimidine.

115) 1-(5-deoxy-1-β-D-ribofuranosyl)-3-phenyl-4-N-(4-ethylphenyl)aminopyrazolo[3,4-d]pyrimidine.

116) 1-(5-deoxy-1-β-D-ribofuranosyl)-3-phenyl-4-N-(4-(2-methylphenyl)aminopyrazolo[3,4-d]pyrimidine.

117) 1-(5-deoxy-1-β-D-ribofuranosyl)-3-phenyl-4-N-(4-ethoxyphenyl)aminopyrazolo[3,4-d]pyrimidine.

118) 1-(5-deoxy-1-β-D-ribofuranosyl)-3-phenyl-4-N-(4-methylphenyl)aminopyrazolo[3,4-d]pyrimidine.

119) 1-(5-deoxy-1-β-D-ribofuranosyl)-3-phenyl-4-N-(4-cyanophenyl)aminopyrazolo[3,4-d]pyrimidine.

120) 1-(5-deoxy-1-β-D-ribofuranosyl)-3-phenyl-4-N-(4-carbamoylphenyl)aminopyrazolo[3,4-d]pyrimidine.

121) 1-(5-deoxy-1-β-D-ribofuranosyl)-3-phenyl-4-N-(4-ethylphenyl)aminopyrazolo[3,4-d]pyrimidine.

122) 1-(5-deoxy-1-β-D-ribofuranosyl)-3-phenyl-4-N-(4-sulfonamidophenyl)aminopyrazolo[3,4-d]pyrimidine.

123) 1-(5-deoxy-1-β-D-ribofuranosyl)-3-phenyl-4-N-(4-acetamidophenyl)aminopyrazolo[3,4-d]pyrimidine.

124) 1-(5-deoxy-1-β-D-ribofuranosyl)-3-(4-methoxyphenyl)-4-N-(henyl)aminopyrazolo[3,4-d]pyrimidine.

EXAMPLE 9

SYNTHESIS OF HETEROCYCLES

The following heterocycles, used as starting materials in this example, and to prepare the corresponding nucleosides in Example 8, were synthesized by procedures analogous to those in Kobayashi, Chem. Pharm. Bull. (Japan), 21, 941 (1973) and Cheng, et al. J. Org. Chem., 21, 1240 (1966).

4-N-(4-Methoxyphenyl)amino-3-phenylpyrazolo[3,4-d]pyrimidine.

4-N-(4-Chlorophenyl)amino-3-phenylpyrazolo[3,4-d]pyrimidine.

4-N-Phenyl)amino-3-(2-thienyl)pyrazolo[3,4-d]pyrimidine.

3-(4-Methylphenyl)-4-N-phenylaminopyrazolo[3,4-d]pyrimidine.

3-(4-Methoxyphenyl)-4-N-phenylaminopyrazolo[3,4-d]pyrimidine.

3-(4-Methoxyphenyl)-4-N-(4-methylphenyl)aminopyrazolo[3,4-d]pyrimidine.

3-(4-Chlorophenyl)-4-N-phenylamionopyrazolo[3,4-d]pyrimidine.

Other heterocycles used for the synthesis of Examples #98–124 can be made by the same procedures.

A. Preparation of 5-Azido-5-deoxy-1-O-methyl-2,3-O-(1-methylethylidene)-D-ribofuranoside (14).

22

A mixture of 1-O-methyl-2,3-O-(1-methylethylidene)-5-O-(4-methylbenzene sulfonyl)-D-ribofuranoside (8.0 g) (Snyder, J.; Serianni, A.; Carbohydrate Research, 163:169 (1987)), dry DMF (40 mL) and $NaN_3$ (4.0 g) was heated at 80 C. for 12 hours. The solvent was evaporated and the residue was chromatographed over silica gel using $CH_2Cl_2$. The fractions containing the faster moving product were pooled and evaporated to obtain 4.8 g (94% yield) of a syrupy product.

B. Preparation of 5-azido-5-deoxy-1,2,3-O-triacetyl-D-ribofuranoside (15).

A solution of 4.6 g (20 mmol) 5-azido-5-deoxy-1-O-methyl-2,3-O-(1-methylethylidene)-D-ribofuranoside (14), in 0.1% $H_2SO_4$ (300 mL) was refluxed for 3 hours. The acid was neutralized (pH ~5) with Amberlite 400 (OH⁻ form) and the resin filtered and washed with ethanol (2×20 mL). The filtrate was evaporated to dryness under high vacuum to give the intermediate compound as a syrupy residue; $^1H$ and $^{13}C$ NMR confirmed the identity of the product as a mixture of α and β anomers. This product (3.1 g, 0.017 mole) was dissolved in 10 ml of pyridine and was treated with acetic anhydride (18 ml). The mixture was stirred for 24 hours and concentrated under vacuum. The residue was dissolved in $CH_2Cl_2$ and the solution washed with 5% $NaHCO_3$. The organic layer was then washed with 0.5 N $H_2SO_4$, dried ($Na_2SO_4$) and evaporated. The residue was filtered through a plug of silica gel ($CH_2Cl_2$) and the filtrate concentrated to afford the title compound, 4.5 g (98% yield) as a semisolid mixture of α and β isomers.

C. Preparation of 5-deoxy-1,2,3-tri-O-acetyl-D-ribofuranoside, (16).

This compound was prepared as described in Snyder, J.; Serianni, A.; Carbohydrate Research, 163:169 (1987).

D. Synthesis of 3-aryl-4-arylaminopyrazolo[3,4-d] pyrimidine nucleosides.

To a slurry of the heterocycle (11) (5.0 mmol) in nitromethane under argon, was added acyl protected ribofuranose(5–7 mmol). The mixture was heated approximately to 80° C. and treated with $BF_3$-etherate (7.0 mmol). The reaction mixture was refluxed gently for 90 minutes, then cooled and evaporated under vacuum. The residue was treated with triethyl amine and water and extracted with methylene chloride. The organic layer was dried over sodium sulfate and evaporated. The residue was chromatographed over silica gel using a gradient of ethyl acetate and hexane as eluting system. The product thus obtained was dissolved in methanol and treated with freshly prepared sodium methoxide solution to adjust the pH to ~10. After stirring the reaction for 2 hours the pH of the solution was adjusted to 4 by adding strongly acidic resin Dowex-120 H⁺ type. The resin was filtered off, washed with methanol and the filtrate was evaporated under reduced pressure. The residue was crystallized from appropriate solvent.

The following compounds were synthesized by the procedures in Examples 8 and 9 (Scheme 2).

89) 4-N-(4-Methoxyphenyl)amino-3-phenyl-1-(5-deoxy-β-D-ribofuranosyl)pyrazolo[3,4-d]pyrimidine. m.p. 165–165.5

90) 4-N-(4-Methoxyphenyl)amino-3-phenyl-1-(5-azido-5-deoxy-β-D-ribofuranosyl)pyrazolo[3,4-d] pyrimidine. m.p. 85.

91) 4-N-(4-Chlorophenyl)amino-3-phenyl-1-(5-deoxy-β-D-ribofuranosyl)pyrazolo[3,4-d]pyrimidine. m.p. 152–153.

92) 4-N-(4-Chlorophenyl)amino-3-phenyl-1-(5-azido-5-deoxy-β-D-ribofuranosyl)pyrazolo[3,4-d]pyrimidine. m.p. 165–167.

93) 3-(4-Methylphenyl)-4-N-phenylamino-1-(5-azido-5-deoxy-β-D-ribofuranosyl)pyrazolo[3,4-d]pyrimidine. m.p. 94–96.

94) 3-(4-Methoxyphenyl)-4-N-phenylamino-1-(5-azido-5-deoxy-β-D-ribofuranosyl)pyrazolo[3,4-d]pyrimidine. m.p. 144–145.

95) 3-(4-Methoxyphenyl)-4-N-(4-methylphenyl)amino-1-(5-azido-5-deoxy-β-D-ribofuranosyl)pyrazolo[3,4-d]pyrimidine. m.p. 100–102.

96) 3-(4-Chlorophenyl)-4-N-phenylamino-1-(5-azido-5-deoxy-β-D-ribofuranosyl)pyrazolo[3,4-d]pyrimidine. m.p. 181–183.

97) 4-N-Phenylamino-3-(2-thienyl)-1-(5-azido-5-deoxy-β-D-ribofuranosyl)pyrazolo[3,4-d]pyrimidine. m.p. 89–92.

It will be readily apparent that many compounds, including those in the formulas above, and in the appended claims, can be made by these various exemplary methods.

UTILITY

The adenosine kinase inhibitors of the present invention may be used in the treatment of a variety of clinical situations where increasing local levels of adenosine are beneficial. The compounds of the invention act as potent inhibitors of adenosine kinase in vitro, and the present compounds in particular are orally available.

Adenosine has been proposed to serve as a natural anticonvulsant. Compounds of the present invention which enhance adenosine levels are useful in seizure disorders, as shown in animal models of seizures detailed below. Adenosine kinase inhibitors may be used in the treatment of patients with seizures or epilepsy or patients who might have chronic low or insufficient adenosine levels or might benefit from increased adenosine such as those suffering from autism, cerebral palsy, insomnia or other neuropsychiatric symptoms.

Adenosine kinase inhibitors of the invention find further utility in the treatment of acute pain, including but not limited to peri-operative, post-surgical, and end-stage cancer pain. Compounds of the invention are also useful in controlling chronic pain, including but not limited to pain caused by arthritis, cancer, trigeminal neuralgia, multiple sclerosis, neuropathies such as those arising from diabetes and AIDS and in addition, lower back pain and phantom limb pain. Treatment of acute and chronic pain can be treated by administration of the compounds of the invention in a systemic or oral fashion, as illustrated by animal models detailed below.

Adenosine has been reported to be an endogenous modulator of inflammation by virtue of its effects on stimulated neutrophil function and on macrophage, lymphocyte and platelet function. The compounds of this invention may therefore be used in treating conditions in which inflammatory processes are prevalent such as arthritis, reperfusion injury, and other inflammatory disorders.

The compounds of the invention are also useful in the treatment of chronic neurodegenerative disease, such as Alzheimer's disease, Parkinson's deisease, ALS, Huntington's disease, and AIDS dimentia.

Stroke and central nervous system ("CNS") trauma are conditions where tissue injury results from reduced blood supply to the CNS and are thus amenable to an intervention that provides increased levels of adenosine to the compromised tissue. It is reported that a significant component of the neurodegeneration resulting from stroke or CNS trauma is caused by increased excitatory amino acid release and sensitivity, which results in neurons being stimulated to death. In addition to vasodilatory properties, adenosine has been reported to inhibit release of excitatory amino acids (Burke and Nadler *J. Neurochem.*, 1988, 51:1541) and responsiveness of neurons to excitation. The compounds of this invention, which increase adenosine levels, may also be used in the treatment of conditions where release of or sensitivity to excitatory amino acids is implicated.

To assist in understanding the present inventions and especially their properties and utilities, the results of a series of experiments are also included. These experiments demonstrated that a number of compounds of the present invention were potent inhibitors of a purified cardiac adenosine kinase. Certain adenosine kinase inhibitors were found to inhibit seizures in a well-established animal model, and exemplary compounds inhibited pain in two other animal models. The results of these studies are set forth in Tables 1–3.

AK INHIBITION

Adenosine kinase activity was measured essentially as described by Yamada et al. *Biochim. Biophys. Acta* 660, 36–43 (1988) with a few minor modifications. Assay mixtures contained 50 mM TRIS-maleate buffer, pH 7.0, 0.1% BSA, 1 mM ATP 1 mM $MgCl_2$, 0.5 µM [U-$^{14}$C]adenosine (400–600 mCi/mmol) and varying duplicate concentrations of inhibitor. The reactions were initiated by addition of approximately 0.1 µU partially purified pig heart adenosine kinase, where one unit is defined as that amount of enzyme required to phosphorylate 1 µmol adenosine per minute. The reactions were incubated for 20 minutes at 37° C. The assay was quenched upon spotting 30 µL aliquots onto 2 $cm^2$ pieces of Whatman DE81 anion exchange paper. The paper squares were washed for 3 minutes in 6 L distilled/deionized water to remove the unreacted adenosine. The washed squares were rinsed in 95% ethanol and dried in an oven at 100° C. for 10 minutes. The amount of $^{14}$C-AMP was quantified by scintillation counting. The concentration of inhibitor required to inhibit 50% of the adenosine kinase activity ($IC_{50}$) was determined graphically. The results for representative compounds of the invention are shown in Table 1.

ANTICONVULSANT ACTIVITY

The anticonvulsant activity of the tested compounds was evaluated in male SA rats (100–150 g, Simonsen) using the maximal electroshock (MES) model described in Swinyard et al., *Antiepileptic Drugs,* 3d Ed. at 85–102 (Levy, et al., eds.), N.Y.: Raven Press (1989). The rats were maintained on a 12/12 light/dark cycle in temperature controlled facilities with free access to food and water. For p.o. administration, the animals are fasted overnight, prior to the experiment. One hour prior to seizure testing, the animals were injected interperitoneally (ip) or orally (per os, po) with one of various doses of test compound dissolved in DMSO or PEG 400.

Maximal electroshock seizures (MES) were induced by administering a 150 mA, 60 Hz current for 0.2 seconds via corneal electrodes using a Wahlquist Model H stimulator. The endpoint measurement was suppression of hind limb tonic extension (HTE), which was judged to occur when any hind leg extension did not exceed a 90 degree angle with the plane of the body. HTE suppression of this kind indicates that the test compound has the ability to inhibit seizures, in theory by inhibiting seizure propagation and spread, if not by raising the seizure threshold (i.e. preventing seizure potential). This endpoint was expressed as the percentage of animals in which the response was inhibited. Typically, compounds were screened initially at one hour following a dose of 5 mg/kg ip. In some cases, the effective dose at which 50% of the rats were protected ($ED_{50}$) was calculated from a dose response curve. The results for exemplary compounds of the invention are in Table 1, expressed as $ED_{50}$ values. For compounds where the $ED_{50}$ was not calculated, the result is >5 if HTE was inhibited in fewer than 50% of the animals in the initial screen, or <5 if HTE was inhibited in more than 50% of the animals in the initial screen.

TABLE 1

UTILITY OF REPRESENTATIVE AK INHIBITORS

| # | AK Inhibition ($IC_{50}$) nM | Anticonvulsant $ED_{50}$ (MES) (mg/kg) ip | po | # | AK Inhibition ($IC_{50}$) nM | Anticonvulsant $ED_{50}$ (MES) (mg/kg) ip | po |
|---|---|---|---|---|---|---|---|
| 4 | 2.0 | 1.1 | 2.1 | 12 | 50.0 | >5 | |
| 1 | 11.0 | 1.9 | 5.1 | 15 | 16.0 | 2.5 | >20.0 |
| 2 | 34.0 | 1.1 | 8.3 | 16 | 9.0 | 2.3 | 8.7 |
| 21 | 14.0 | 1.1 | >20.0 | 17 | 17.0 | 10 | >10.0 |
| 27 | 1.0 | 0.7 | 3.2 | 18 | 4.0 | 3.8 | >40.0 |
| 86 | 4.5 | 12.30 | >20.0 | 19 | 2.0 | 0.4 | >30.0 |
| 87 | 4.5 | 2.31 | >2.3 | 20 | 32.0 | 5.5 | 40.0 |
| 88 | 5.0 | 2.62 | >2.6 | 21 | 250.0 | >20.0 | |
| 89 | 17.0 | 5 | | 23 | 75.0 | 5 | >10.0 |
| 91 | 11.0 | >10 | | 40 | 2.0 | 5 | >10.0 |
| 90 | 8.0 | >3.4 | | 24 | 1.0 | 2.5 | 10.0 |
| 92 | 17.0 | | | 25 | 10.0 | 3.1 | |
| 97 | 10.0 | >5 | | 24 | 5.0 | 1.7 | |
| 93 | 20.0 | >5 | | 11 | 4.0 | 5 | |
| 33 | 46.0 | 5 | | 10 | 1.0 | 5 | |
| 94 | 3.0 | >5 | | 28 | 4.0 | <5 | |
| 13 | 6.0 | 2 | >10.0 | 29 | 20.0 | >5 | |
| 95 | 7.0 | >5 | | 30 | 28.0 | >5 | |
| 96 | 15.0 | >5 | | 41 | 42.0 | >5 | |
| 35 | 4.0 | 5.0 | | 42 | 8.0 | >5 | |
| 36 | 7.2 | >10.0 | | 31 | 2.0 | >5 | |
| 37 | 0.8 | 20.0 | >4.0 | 34 | 5.0 | 5 | |
| 38 | 30.0 | >5 | | 32 | 0.5 | 5 | >5 |
| 3 | 19.0 | 7.1 | >20.0 | 43 | 3.0 | <5 | |
| 39 | 5.0 | 1.7 | >40.0 | | | | |

ANALGESIC ACTIVITY

Analgesic activity of representative compounds of the invention was evaluated in male SA rats (100–150 g, Simonsen) using the hot plate and tail flick models of pain, similar to those described in Sosnowski et al., *J. Pharmacol. Exper. Ther.*, 250:3, 915–922 (1989). See also, *Life Sciences* 51:171–76 (1992). These models measure pain avoidance and tolerance in response to a regulated stimulus, and compare the response of animals before and after they are given test compound.

The tail flick response is evoked by placing the tail of a rat over a focused beam of light. The latency or response time to flick the tail away from the incident heat source was recorded electronically by an appropriate measuring device, for example an apparatus manufactured by Ugo Baslie. Longer times indicate greater tolerance to the thermally induced pain stimulus. The maximum exposure time is limited to avoid tissue damage (8 seconds), in the event a rat does not respond to the stimulus within a predetermined period. In this experiment, the rats were accommodated to the hand restraint of the testing to prevent spurious movements from causing false responses. A mark was made on the dorsal surface of each tail approximately 3–5 cm from the tip to ensure testing at the same location on the tail.

In the hot plate model, a rat is placed on a heated metal plate (typically 50 C). The endpoint of this evaluation is the time required for the rat to lick its hind paw. A predetermined cutoff time (60 seconds) is used to protect the animals from injury, in the event there is no response. Three tests were performed 15 minutes apart prior to dosing; these tests serve as the baseline for each animal. Rats were gavaged with one of the various doses and the tail flick and hot plate responses were monitored at various times, e.g. 30, 60, 120, 240, and 480 minutes after garage.

Dose response curves for each compound in the tail flick and hot plate tests are made by plotting the dose against the normalized peak response, or maximum possible effect (MPE). The MPE is calculated as $$\frac{(\text{test latency} - \text{baseline latency})}{(\text{cutoff latency} - \text{baseline latency})} \times 100\%.$$

The effective dose at which 50% of the rats were protected ($ED_{50}$) was calculated from the dose response curve using linear regression analysis. Results for representative compounds according to the invention are set forth in Table 2.

ANTI-INFLAMMATORY ACTIVITY

Carrageenan (Type λ) was suspended in sterile PBS at 1% (w/v), autoclaved for 30 minutes, and stored at room temperature. Rats were pretreated with vehicle or AK inhibitor (10 mg/kg) by oral gavage or i.p. administration and the volume of the left hind paw was measured using a water displacement plethysmometer (Stoelting Co., Wood Dale, Ill.). One hour after oral treatment or 30 minutes after i.p. treatment, the rats were briefly anesthetized, and 0.1 ml of the carrageenan solution was injected subcutaneously into the planar surface of the left hind paw. The ensuing paw swelling was measured by plethysmometry after 3 hours. The paw volume in millileters was subtracted from the pre-injection paw volume. Data are presented as the percent inhibition of paw swelling in AK inhibitor treated animals, compared to vehicle treated control animals. Rosengren et al., *J. Immunology* 154:5444–51 (1995).

TABLE 2

ANALGESIC AND ANTI-INFLAMMATORY UTILITY

| | Analgesic $ED_{50}$ (mg/kg) | | | | Carrageenan |
|---|---|---|---|---|---|
| | Hot Plate | | Tail Flick | | Paw (% inh) |
| | ip | po | ip | po | po |
| 4 | 3.9 | | 7.4 | | 19.6 |
| 1 | | 16.9 | | <10 | 0.2 |
| 2 | | 7.3 | | 14.1 | 18.4 |
| 27 | | | | | 49.5 |
| 37 | | | | | 26.0 |
| 24 | | | | | 21.3 |
| 28 | | | | | 31.0 |
| 29 | | | | | 10.7 |
| 42 | | | | | 12.3 |
| 31 | | | | | -5.8 |
| 34 | | | | | -0.2 |

ORAL BIOAVAILABILITY

Oral bioavailability was determined by comparing the dose corrected areas under the plasma-concentration time curve (AUC) to infinity for the each tested compound, given orally and intravenously in dogs.

For each compound, two female beagles were fasted overnight and received an intravenous infusion of test compound in a 10 mg/ml solution of PEG-400 via a cephalic vein. One dog received this solution at an infusion rate of 0.1 mL/min for 20 minutes. The other dog received a 0.2 mL/in infusion for 10 minutes. Heparinized blood was obtained from the other cephalic vein at predetermined time points during the infusion (0 [pre-dose], 5, 10, 15, and 20 minutes for the 20 min. infusion and 0, 5 and 10 minutes for the 10 min. infusion). After the infusion, heparinized blood was obtained at 5, 10, 15, 30, 45 min., and 1, 1.5, 2, 4, 6, 8, and 24 hours post infusion. The plasma was separated within 10 minutes of blood collection and was stored frozen. The plasma concentration of compound was then determined for these IV infusions.

Another two female beagles also fasted overnight, received 10 mg/kg of compound solution via a stomach tube, followed by a 6 ml rinse of the tube with PEG-400. Blood samples were handled as for the IV experiments, with samples taken at 0 [pre-dose], 15, 30 and 45 minutes and 1, 1.5, 2, 4, 6, 8, and 24 hours after administration. The plasma concentration of compound was determined for this oral administration.

The samples were assayed for intact adenosine kinase inhibitor by high performance liquid chromatography (HPLC). An internal standard was added to each test sample and standard sample. Each was then extracted with 10 volumes of 1% v/v dimethylsulfoxide in acetonitrile. After vigorous vortexing, the mixture was centrifuged and the supernatant was evaporated to dryness under nitrogen at 50 C. The dried residue was reconstituted in mobile phase and the contents were analyzed for the adenosine kinase inhibitor (AKI) on HPLC.

HPLC was performed on a Beckman Ultrasphere C18 reverse phase column (4.6×150 mm) eluted isocratically at ambient temperature with a mobile phase of 60–70% methanol at a flow rate of 1.5 ml/min. The eluant was monitored by UV absorbance at 300 nm. Pharmacokinetic parameters were calculated from the plasma concentration vs. time data, using standard non-compartmental methods. Giraldi et al., *Pharmacokinetics.*, 2d ed. Marcel Dekker, N.Y. (1983). After normalization to account for the different amounts of compound given, the oral bioavailability is calculated as the normalized oral AUC divided by the IV AUC ×100%.

Results for representative compounds of the invention are shown in Table 3.

TABLE 3

| Compound | % Oral Availability |
|---|---|
| 4 | 8 |
| 1 | 60 |
| 2 | 47 |
| 21 | 23 |
| 27 | 100 |

LIVER TOXICITY

Female SA rats (150–200 g) were anesthetized with halothane and cannulated via the internal jugular vein. The animals wee allowed to recover for 3 days. At this time, 37.5 µmole/kg of an AK inhibitor was dissolved in 75% PEG400 and infused through the jugular catheter over 20 minutes. Twelve hours later, an additional 37.5 µmole/kg was infused over 20 minutes (total dose=75 µmole/kg). Twelve hours after the second dose, the animals were anesthetized with halothane and exsanguinated through the inferior vena cava. Liver enzymes (serum glutamic-oxaloacetic transaminase (SGOT), serum glutamic-pyruvic transaminase (SGPT), alkaline phosphatase) and total bilirubin in the serum samples were dermined by a commercial laboratory. Results are shown in Table 4.

TABLE 4

LIVER TOXICITY

| # | Total Bilirubin (mg/dL) | | SGOT (IU/L) | | SGPT (IU/L) | | Alkaline (IU/L) Phosphatase | |
|---|---|---|---|---|---|---|---|---|
| Vehicle | 0.10 | ±0.04 | 59 | ±3 | 42 | ±0 | 140 | ±50 |
| REF. A | 0.76 | | 508 | | 76 | | 163 | |
| REF. B | 0.30 | | 100 | | 41 | | 113 | |
| 1 | 0.08 | | 51 | | 20 | | 96 | |
| 2 | 0.13 | | 95 | | 38 | | 128 | |
| 27 | 1.03 | | 388 | | 70 | | 93 | |

REF A. 4-amino-5-iodo-7-(5-deoxy-1-β-D-ribofuranosylpyrrolo[2,3-d]pyrimidine

REF B. 4-amino-1-(5-amino-5-deoxy-1-β-D-ribofuranosyl)-3-bromopyrazolo[3,4-d]pyrimidine HCL

FORMULATIONS

Compounds of the invention are administered to the affected tissue at the rate of from 0.1 to 200 nmole/min/kg, preferably from 1 to 50 nmol/min/kg. Such rates are easily maintained when soluble compounds are intravenously administered as discussed below. When other methods are used (e.g., oral administration), use of time-release preparations to control the rate of release of the active ingredient may be preferred. These compounds are administered in a dose of about 0.01 mg/kg/day to about 100 mg/kg/day, preferably from about 0.1 mg/kg/day to about 10 mg/kg/day.

For the purposes of this invention, the compounds of the invention may be administered by a variety of means including orally, parenterally, by inhalation spray, topically, or rectally in formulations containing conventional non-toxic pharmaceutically acceptable carriers, adjuvants and vehicles. The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including those from the group consisting of sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol arthydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophylized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as Oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 1000 µmoles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 0.1 to about 15 µmoles of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous with the compounds of formula (I) as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the ddPN ingredient such carriers as are known in the art to be appropriate.

Formations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine kinase inhibitor compound. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Capsules comprising adenosine kinase inhibitors suitable for oral administration according to the methods of the present invention may be prepared as follows: (1) for a 10,000 capsule preparation: 1500 g of adenosine kinase inhibitor is blended with other ingredients (as described above) and filled into capsules which are suitable for administration depending on dose, from about 4 capsules per day (1 per 6 hours) to about 8 capsules per day (2 capsules per 6 hours), to an adult human.

The compounds of this invention and their preparation and use can be understood further by the representative examples above, which illustrate the various aspects of the invention without limiting its scope.

We claim:

1. A compound according to the formula

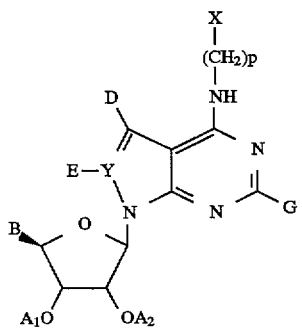

wherein:

$A_1$ and $A_2$ are each independently hydrogen, acyl, or taken together form a cyclic carbonate;

B is alkenyl, or $(CH_2)_n$—B', where n is from 1 to 4 and B' is hydrogen, hydroxy, alkyl, alkoxy, amino, azido, or halogen;

D is halogen, aryl, aralkyl, alkynyl, haloalkyl, cyano, or carboxamido;

Y is carbon or nitrogen;

E is nothing when Y is nitrogen, and is hydrogen, halogen or alkyl when Y is carbon;

G is hydrogen or halogen;

p is from 0 to 3;

and X is a five or six member aryl ring, optionally substituted at any one or more positions by hydroxy, amino, alkyl, alkoxy, per halo lower alkyl, sulfonamide, halogen, cyano, or CONRR', NRCOR', NRR', or SR where R and R' are independently hydrogen or lower alkyl;

and pharmaceutically acceptable salts thereof.

2. A compound of claim 1, where X is a six-membered ring.

3. A compound of claim 1, where X is a six-membered ring, substituted in the para position.

4. A compound of claim 3, where X is phenyl, substituted in the para position by a halogen.

5. A compound of claim 4, where the halogen is fluorine.

6. A compound of claim 1, where X is a six-membered ring and D is aryl.

7. A compound of claim 1, where X is substituted phenyl and D is aryl.

8. A compound of claim 1, where X is phenyl substituted at the para position and D is aryl.

9. A compound of claim 1, where X is phenyl substituted at the para position by halogen, and D is aryl.

10. A compound of claim 9, where the halogen is fluorine and D is optionally substituted phenyl.

11. A compound of claim 1, where G and each A is hydrogen.

12. A compound of claim 11, where X is a six-membered ring.

13. A compound of claim 11, where X is a six-membered ring substituted at the para position.

14. A compound of claim 13, where X is phenyl substituted at the para position by halogen.

15. A compound of claim 14, where D is aryl.

16. A compound of claim 15, where p is 0, D is phenyl and the halogen is fluorine.

17. A compound of claim 1, where G and each A is hydrogen and B is one of $CH_3$ and $CH_2OH$.

18. A compound of claim 17, where X is a six-membered ring.

19. A compound of claim 17, where X is a six-membered ring substituted at the para position.

20. A compound of claim 19, where X is phenyl substituted at the para position by halogen.

21. A compound of claim 20, where D is aryl.

22. A compound of claim 21, where D is phenyl and the halogen is fluorine.

23. A compound of claim 1, where Y is carbon.

24. A compound of claim 1, where Y is carbon and E is hydrogen.

25. A compound of claim 1, where Y is carbon, and E, G and each A are hydrogen.

26. A compound of claim 25, where X is a six-membered ring.

27. A compound of claim 25, where X is a six-membered ring substituted at the para position.

28. A compound of claim 27, where X is phenyl substituted at the para position by halogen.

29. A compound of claim 28, where D is aryl.

30. A compound of claim 29, where D is phenyl and the halogen is fluorine.

31. A compound according to the formula $$\begin{array}{c}
X \\
| \\
(CH_2)p \\
| \\
D \quad NH \\
\diagdown \diagup \quad \diagup \\
\quad \quad N \\
E-Y \quad \quad \parallel \\
\diagup \quad \diagdown \quad N \diagdown C-G \\
B \quad N \\
\diagdown \diagup O \diagdown \diagup \\
A_1O \quad OA_2
\end{array}$$

wherein:

A₁ and A₂ are hydrogen;

B is $(CH_2)_n$—B' where n is from 1 to 2 and B' is hydrogen, hydroxy, alkoxy or amino;

D is halogen or aryl;

Y is carbon or nitrogen;

E is nothing when Y is nitrogen, and is hydrogen or halogen when Y is carbon;

G is hydrogen or halogen;

p is from 0 to 1;

and X is a five or six member aryl ring, optionally substituted at any one or more positions by alkyl, alkoxy, per halo lower alkyl, sulfonamide, halogen, cyano, carboxamido, acylamino, NRR', or SR where R and R' are independently hydrogen or lower alkyl;

and pharmaceutically acceptable salts thereof.

32. A compound of claim 31, where Y is carbon.

33. A compound of claim 32, where E, G, and each A are hydrogen.

34. A compound of claim 33, where B is methyl.

35. A compound of claim 32, where p is 0 and X is a six-membered ring substituted at the para position.

36. A compound of claim 32, where D is aryl.

37. A compound of claim 32, where D is aryl, p is 0, and X is a six-membered sing substituted at the para position.

38. A compound of claim 32, where D is phenyl, p is 0, and X is phenyl substituted at the para position by a halogen.

39. A compound of claim 38, where the halogen is fluorine.

40. A compound of claim 31, where Y is nitrogen.

41. A compound of claim 40, where G and each A are hydrogen.

42. A compound of claim 40, where D is aryl.

43. A compound of claim 40, where D is aryl, and G and each A are hydrogen.

44. A compound of claim 43, where p is 0.

45. A compound of claim 44, where D is phenyl and X is a six-membered ring substituted at the para position with halogen.

46. A compound of the formula $$\begin{array}{c}
J \\
\diagup \diagdown \quad J' \\
\parallel \quad \parallel \\
\diagdown \diagup \\
| \\
(CH_2)p \\
| \\
D \quad NH \\
\diagdown \diagup \quad \diagup \\
\quad \quad N \\
E-Y \quad \parallel \\
\diagup \quad \diagdown \quad N \diagdown \diagup \\
B \quad N \\
\diagdown \diagup O \diagdown \diagup \\
HO \quad OH
\end{array}$$

wherein

B is CH₂OH, or CH₃;

D is a five or six-membered ring;

E is nothing when Y is nitrogen and is hydrogen or halogen when Y is carbon;

Y is carbon or nitrogen;

and J and J' are independently halogen, hydrogen, cyano, alkoxy, alkyl, amino, carboxamido, acylamino, or SR, where R is hydrogen or lower alkyl.

47. A compound of claim 46 where B is CH₃.

48. A compound of claim 46 where Y is nitrogen.

49. A compound of claim 46 where Y is carbon.

50. A compound of claim 49 where D is phenyl.

51. A compound of claim 1 where X is a six membered ring p is 0 or 1.

52. A compound of claim 1, where D is aryl or halogen.

53. A compound of claim 1 where D is aryl.

54. A compound of claim 53 where D is substituted phenyl.

55. A compound of claim 46, where each J is independently halogen or hydrogen.

56. A compound of claim 50, where J is fluoro, J' and E are hydrogen, and B is methyl.

57. A compound of claim 49, where D is parafluorophenyl, J is fluoro, J' and E are hydrogen, and B is methyl.

* * * * *